United States Patent [19]

Boden et al.

[11] Patent Number: 4,568,538

[45] Date of Patent: Feb. 4, 1986

[54] FLAVORING WITH NORBORNYL PYRIDINE DERIVATIVES

[75] Inventors: Richard M. Boden, Ocean; Claude Grim, Keansburg, both of N.J.

[73] Assignee: International Flavors & Fragrances Inc., New York, N.Y.

[21] Appl. No.: 742,717

[22] Filed: Jun. 7, 1985

Related U.S. Application Data

[62] Division of Ser. No. 582,756, Feb. 23, 1984, Pat. No. 4,539,143.

[51] Int. Cl.$^4$ .................. A23L 1/226; A23L 1/235
[52] U.S. Cl. .................................. 424/49; 426/3; 426/537; 514/788
[58] Field of Search ............ 426/3, 537; 424/49; 514/788

[56] References Cited

U.S. PATENT DOCUMENTS 3,716,543 2/1973 Hall .................... 426/537

Primary Examiner—Joseph Golian
Attorney, Agent, or Firm—Arthur L. Liberman

[57] ABSTRACT

Described are norbornyl pyridine derivatives defined according to the generic structure:

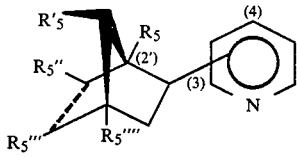

wherein $R_5$, $R_5'$, $R_5''$, $R_5'''$ each represents hydrogen or methyl with the proviso that at least four of $R_5$, $R_5'$, $R_5''$, $R_5'''$ and $R_5''''$ represent hdyrogen; wherein the dashed line represents a carbon-carbon single bond or a carbon-carbon double bond and wherein the pyridinyl moiety is bonded to the norbornyl moiety at the 2' position of the norbornyl moiety and at either the 2 or the 4 position of the pyridinyl moiety as well as organoleptic uses thereof in augmenting or enhancing the aroma or taste of foodstuffs, chewing gums, toothpastes, chewing tobaccos, medicinal products, perfume compositions, colognes and perfumed articles including, but not limited to solid or liquid anionic, cationic, zwitterionic and nonionic detergents, cosmetic compositions, fabric softener compositions, fabric softener articles, hair preparations, and perfumed polymers. Also described are processes for preparing such compounds comprising reacting vinyl pyridines defined according to the structure:

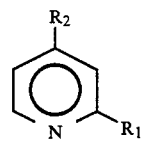

wherein one of $R_1$ and $R_2$ is hydrogen and the other of $R_1$ and $R_2$ is vinyl with a bicyclopentadiene derivative defined according to the structure:

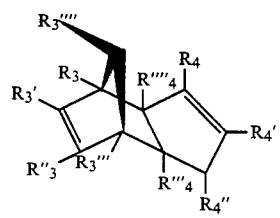

wherein $R_3$, $R_3'$, $R_3''$, $R_3'''$ and $R_3''''$ each represents hydrogen or methyl with the proviso that at least four of $R_3$, $R_3'$, $R_3''$, $R_3'''$ and $R_3''''$ represent hydrogen and wherein $R_4$, $R_4'$, $R_4''$, $R_4'''$ and $R_4''''$ each represents hydrogen or methyl with at least four of $R_4$, $R_4'$, $R_4''$, $R_4'''$ and $R_4''''$ representing hydrogen and then as desired hydrogenating the resulting product.

2 Claims, 14 Drawing Figures

GLC PROFILE FOR EXAMPLE I.
CRUDE

GLC PROFILE FOR EXAMPLE II.
CRUDE

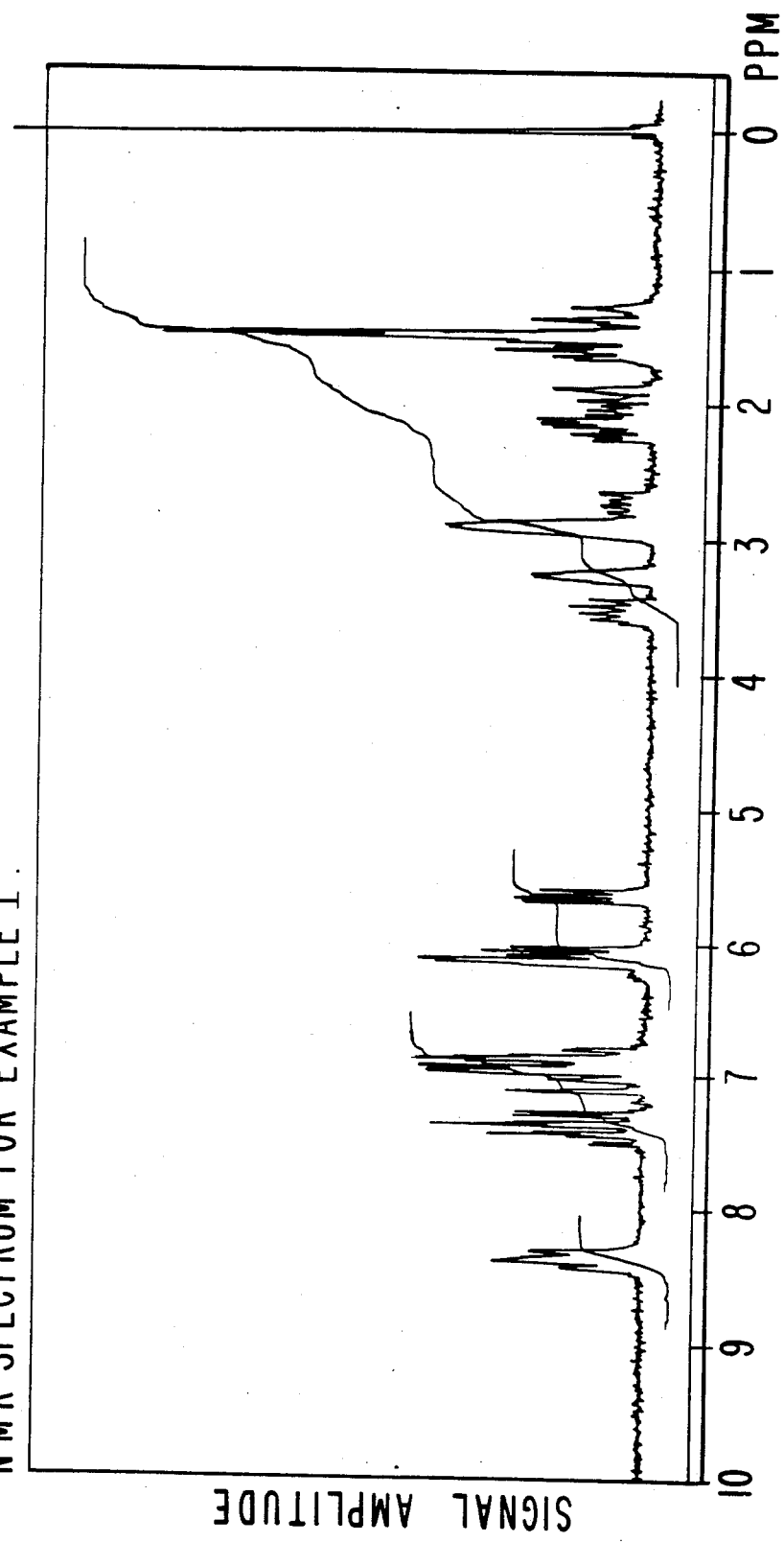

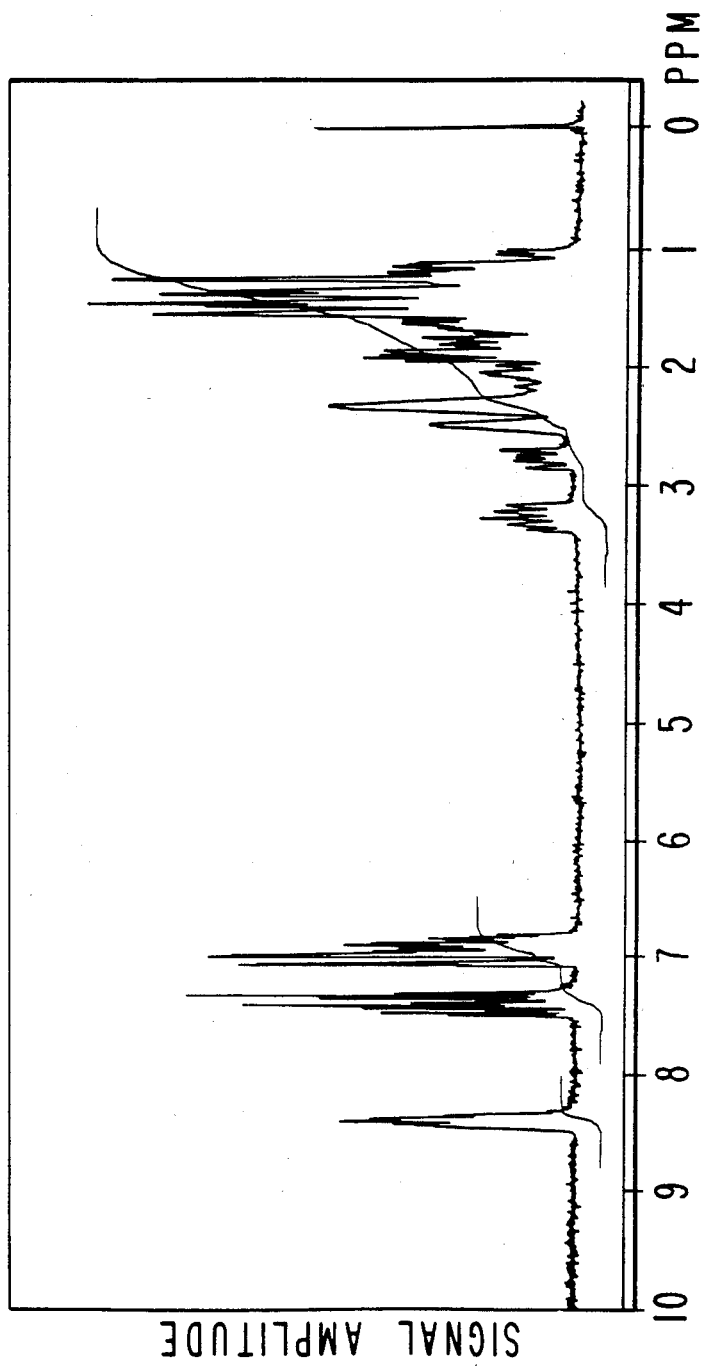

GLC PROFILE FOR EXAMPLE III. CRUDE

GLC PROFILE FOR EXAMPLE IV. CRUDE

NMR SPECTRUM FOR FRACTION 6 OF EXAMPLE III.

NMR SPECTRUM FOR EXAMPLE IV.

FIG. 9
GLC PROFILE FOR EXAMPLE V.
CRUDE
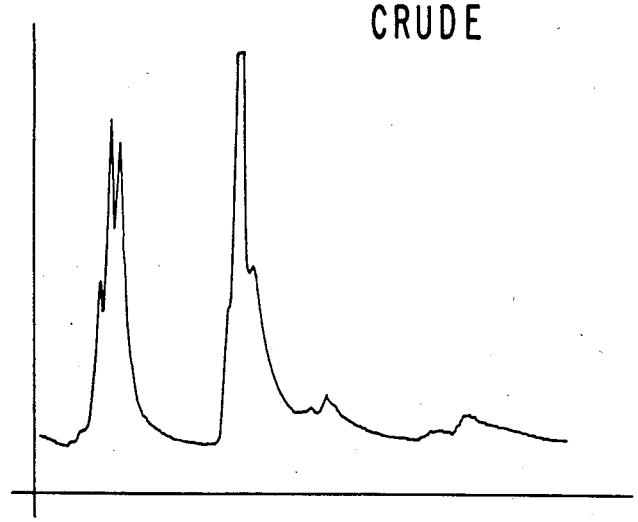
FIG. II
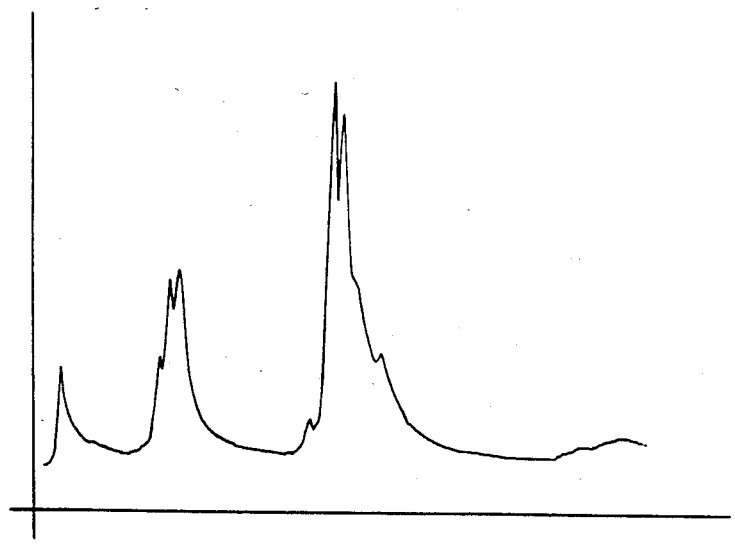
GLC PROFILE FOR EXAMPLE VI.
CRUDE

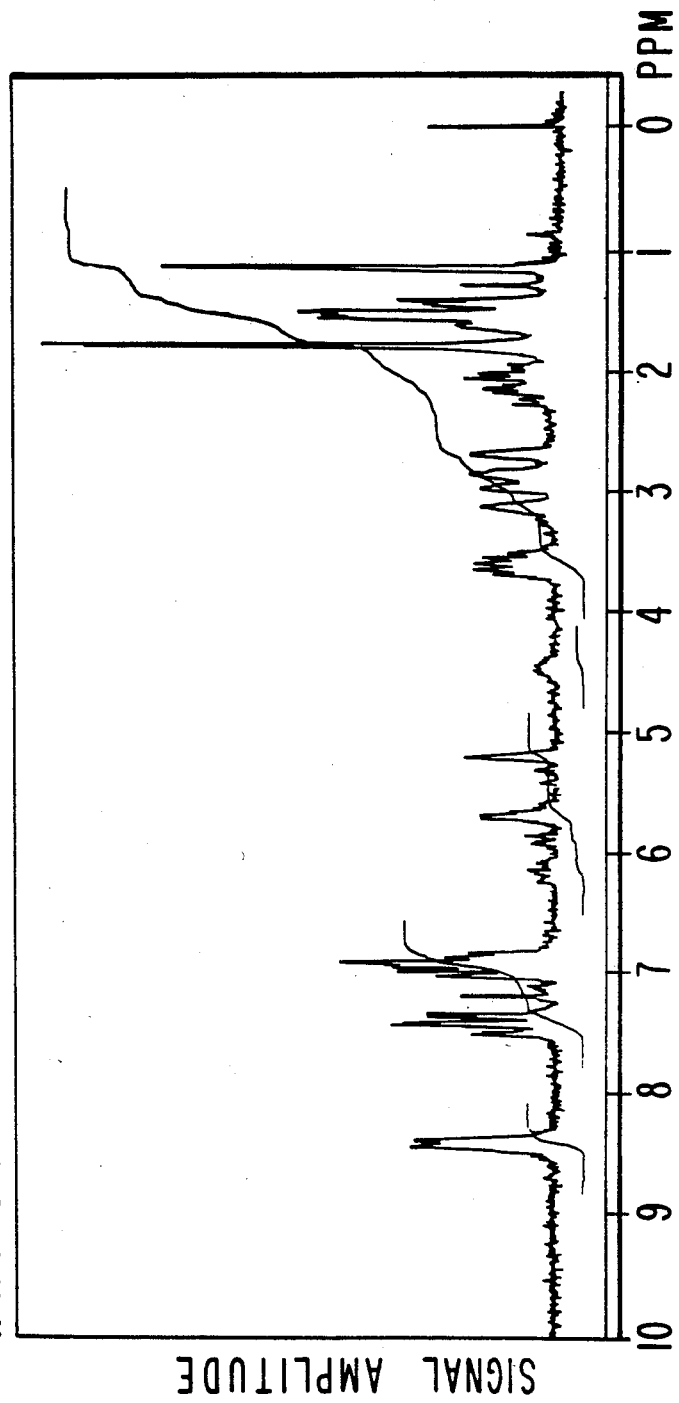

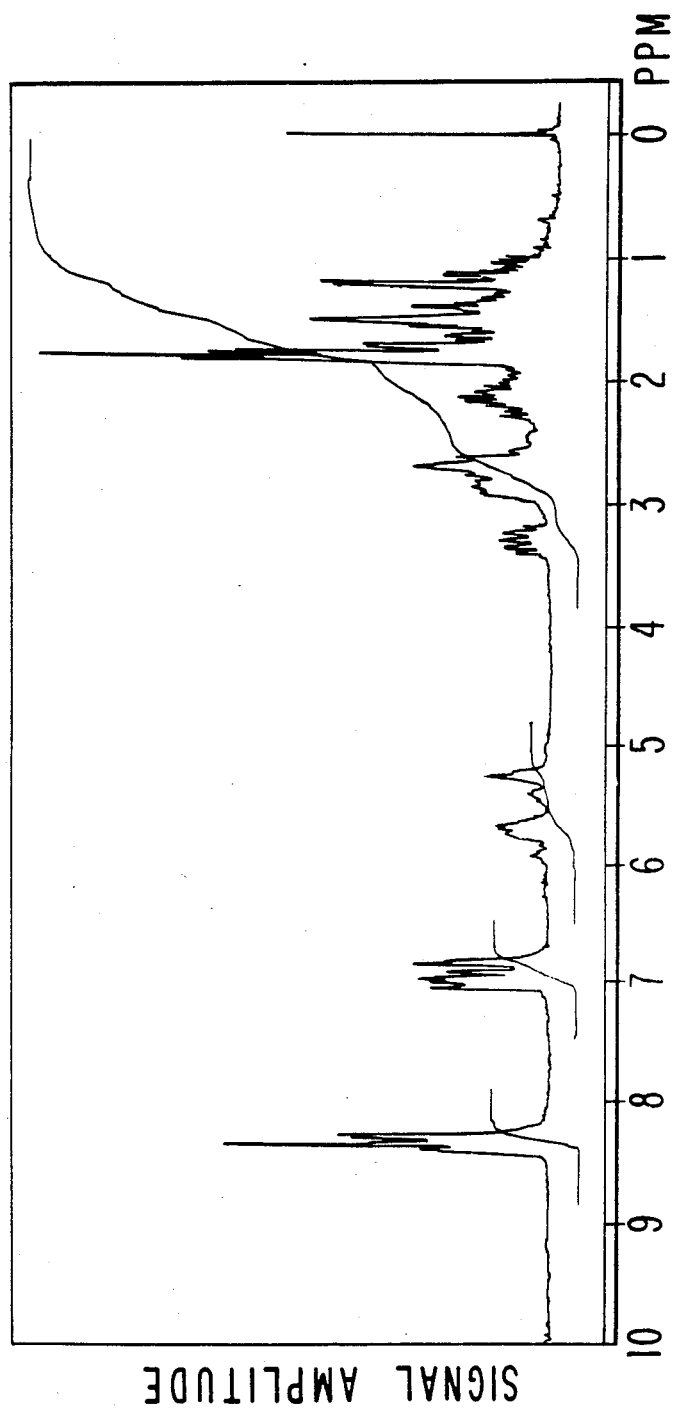
FIG.12 NMR SPECTRUM FOR EXAMPLE VI

FLAVORING WITH NORBORNYL PYRIDINE DERIVATIVES

This is a divisional of application Ser. No. 582,756, filed Feb. 23, 1984, now U.S. Pat. No. 4,539,143.

BACKGROUND OF THE INVENTION

There is a continuing search for materials having desirable fragrance and organoleptic properties. Such materials are sought either to replace costly natural materials or to provide new food flavors, fragrances, perfume types or flavor nuances which have not, heretofore, been available.

Especially desirable qualities for substances having interesting fragrances and flavors are stability in a wide variety of perfumed articles, perfume compositions and foodstuffs, ease of manufacture, intensity and pleasantness of aroma and intensity of pleasantness of flavor.

Particularly desirable are in the perfume, cologne and perfumed article area are fragrance nuances which can be described as petitgrain-like, neroli-like, verdima-like, green, herbaceous, galbanum-like, musk, amber, woody, rose, minty, cedarleaf, eucalyptus, bergamot, orris-like and balsamic-like with amber-like, woody, musk, rose, green, herbaceous, leafy, minty and vanoris-like undertones.

Particularly desirable in the food flavor, chewing gum flavor, toothpaste flavor, medicinal product flavor and chewing tobacco flavor areas are flavors which can be described as bell pepper-like, green vegetable, galbanum-like, floral, pear-like, peach-like, walnut-like, green, orange-albedo, minty, cinnamon-like and bitter chocolate-like, insofar as their aromas and tastes are concerned.

Terpinyl pyridine derivatives have been previously described in the organoleptic industry, for example, United States Letters Patent, Ser. No. 3,716,543 issued on Feb. 13, 1973 discloses compounds defined according to the structures:

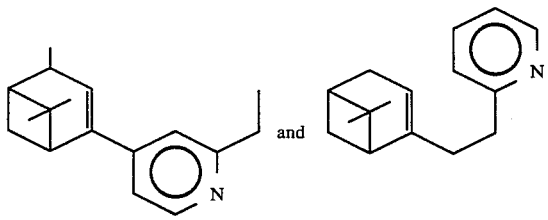

and implicitly includes in its genus the compound having the structure:

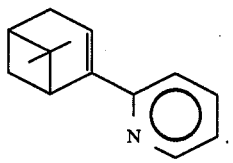

Norbornyl pyridine derivatives defined according to the structures:

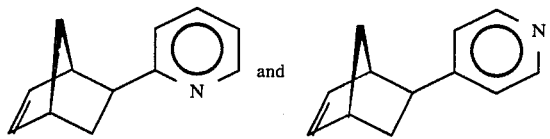

are disclosed as intermediates useful for the preparation of hypotensive agents which are bisquaternary ammonium salts.

Nothing in the prior art, however, discloses the genus of compounds defined according to the structure:

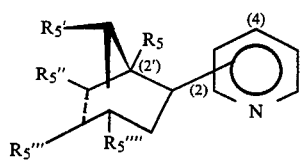

wherein the dashed line represents a carbon-carbon single bond or a carbon-carbon double bond and wherein $R_5$, $R_5'$, $R_5''$, $R_5'''$ and $R_5''''$ represents hydrogen or methyl with at least four of $R_5$, $R_5'$, $R_5''$, $R_5'''$ and $R_5''''$ being hydrogen and wherein the bond between the pyridinyl moiety and the norbornyl moiety leading from the 2' position of the norbornyl moiety is located at the pyridinyl moiety at either the 2 position or the 4 position thereof for augmenting or enhancing the aroma or taste of foodstuffs, chewing gums, chewing tobaccos, toothpastes, medicinal products, perfume compositions, colognes and perfumed articles. Nothing in the prior art discloses such compounds as useful as hypotensive agents and as anti-stress agents.

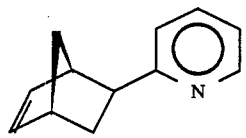

(Conditions: SE-30 column programmed at 100°–220° C. at 8° C. per minute).

FIG. 2 is the NMR spectrum for the compound having the structure:

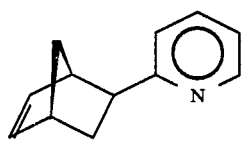

produced according to Example I ("endo":"exo" isomer ratio about 55:45. Conditions: Field strength: 100 MHz; solvent: CFCl₃).

Figure 3:
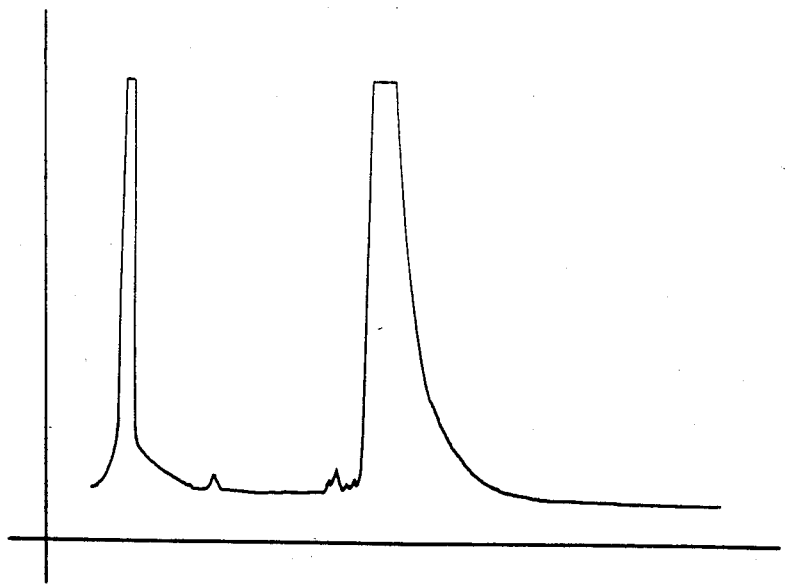

FIG. 3 is the GLC profile for the crude reaction product of Example II containing the compound having the structure:

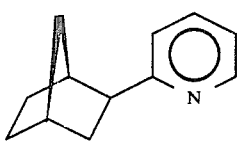

(Conditions: Carbowax column programmed at 100°–220° C. at 8° C. per minute).

FIG. 4 is the NMR spectrum for fraction 1 of the distillation product of the reaction product of Example II containing the compound having the structure:

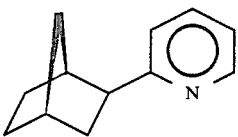

(Conditions: Field strength: 100 MHz; solvent: CFCl₃).

Figure 5:
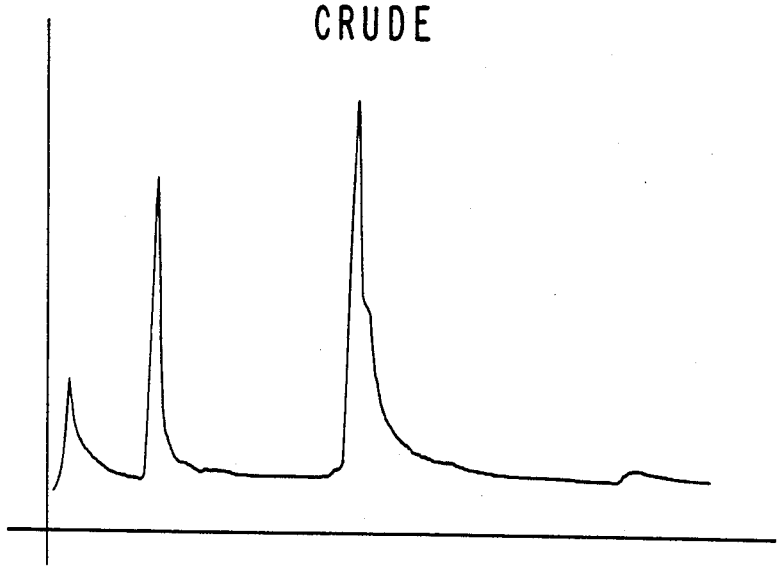

FIG. 5 is the GLC profile for the crude reaction product of Example III containing the compound having the structure:

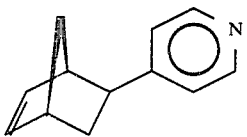

(Conditions: SE-30 column programmed at 100°–220° C. at 8° C. per minute).

Figure 6:
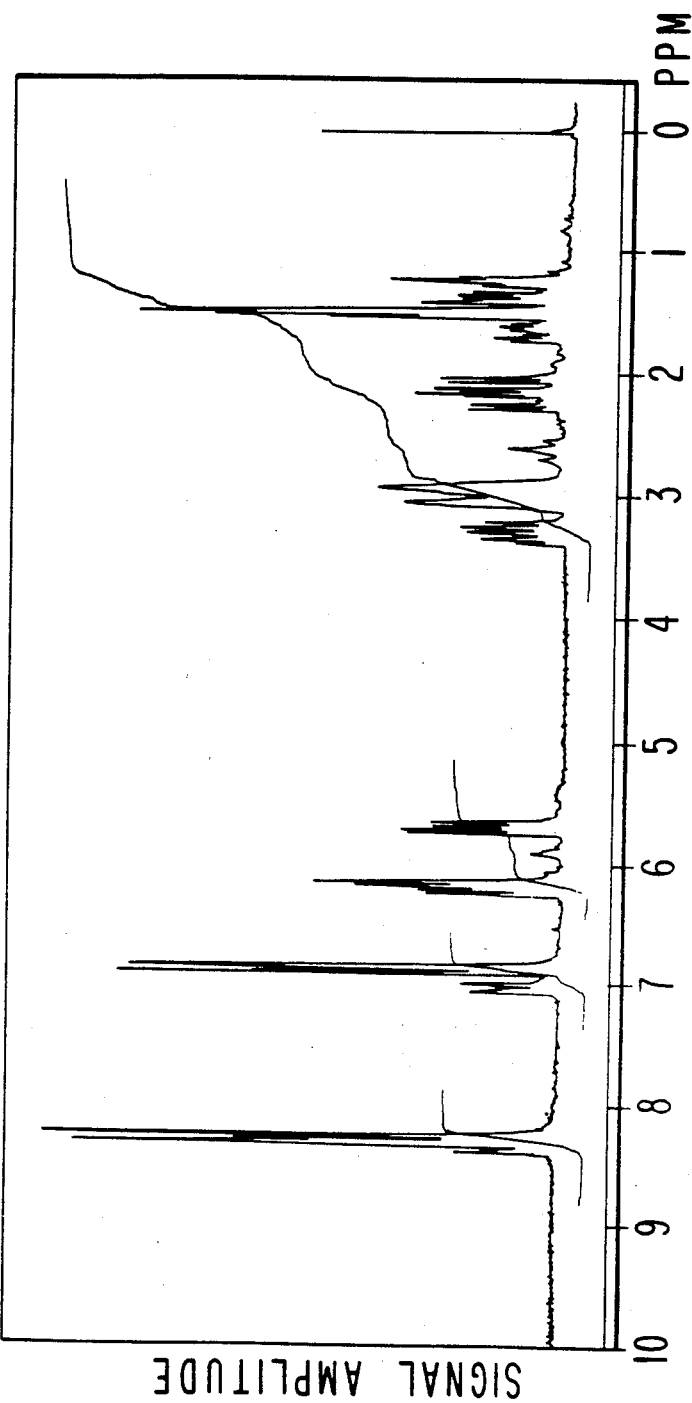

FIG. 6 is the NMR spectrum for fraction 6 of the distillation product of the reaction product of Example III containing the compound having the structure:

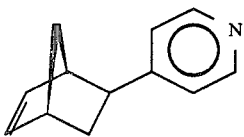

(Conditions: Field strength: 100 MHz; solvent: CFCl₃).

Figure 7:
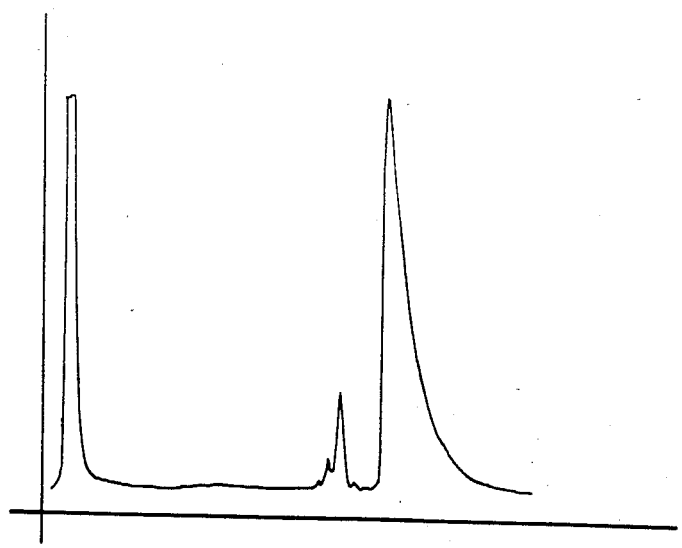

FIG. 7 is the GLC profile for the crude reaction product of Example IV containing the compound having the structure:

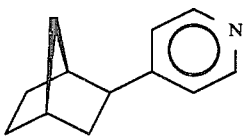

(Conditions: Carbowax column programmed at 100°–220° C. at 8° C. per minute).

Figure 8:
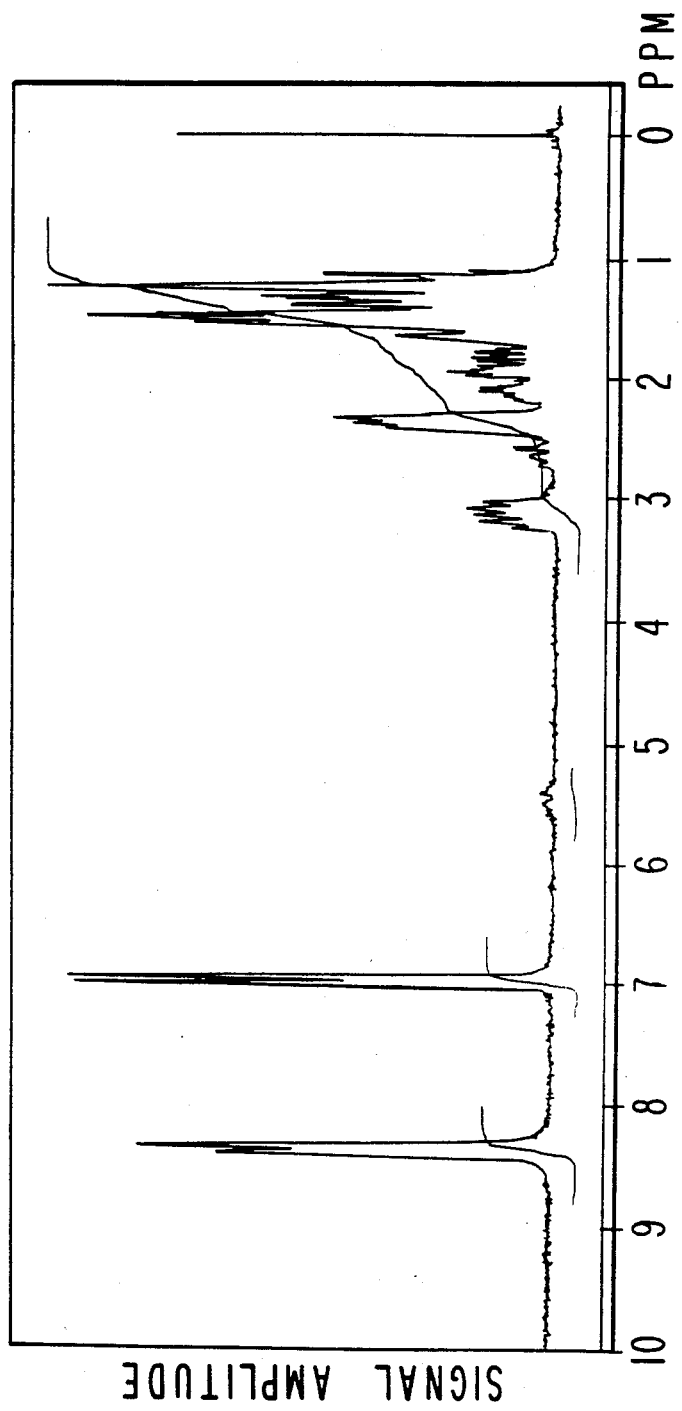

FIG. 8 is the NMR spectrum for the compound having the structure:

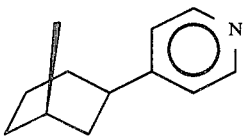

produced according to Example IV (Conditions: Field strength 100 MHz; solvent: CFCl₃).

FIG. 9 is the GLC profile for the crude reaction product of Example V containing a mixture of compounds defined according to the structures:

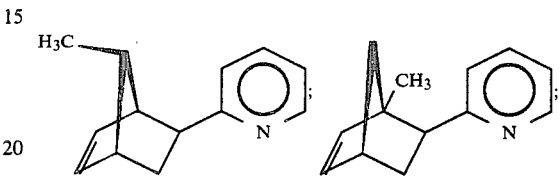

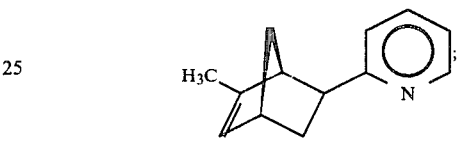

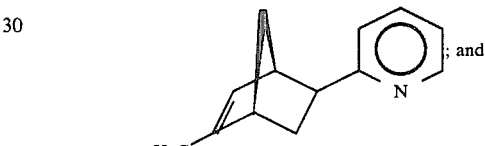

; and

or broadly defined according to the structure:

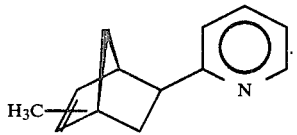

FIG. 10 is the NMR spectrum for the mixture of compounds defined according to the structure:

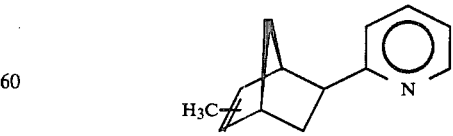

produced according to Example V (Conditions: Solvent: CFCl₃; field strength: 100 MHz).

FIG. 11 is the GLC profile for the crude reaction product of Example VI containing a mixture of compounds defined according to the structure:

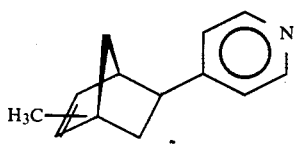

(Conditions: SE 30 column programmed at 100°–220° C. at 8° C. per minute).

FIG. 12 is the NMR spectrum for fraction 5 of the distillation product of the reaction product of Example VI containing a mixture of compounds defined according to the structure:

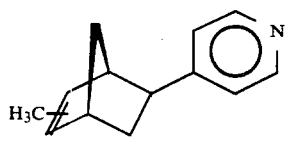

(Conditions: Field strength: 100 MHz; solvent: $CFCl_3$).

Figure 13:
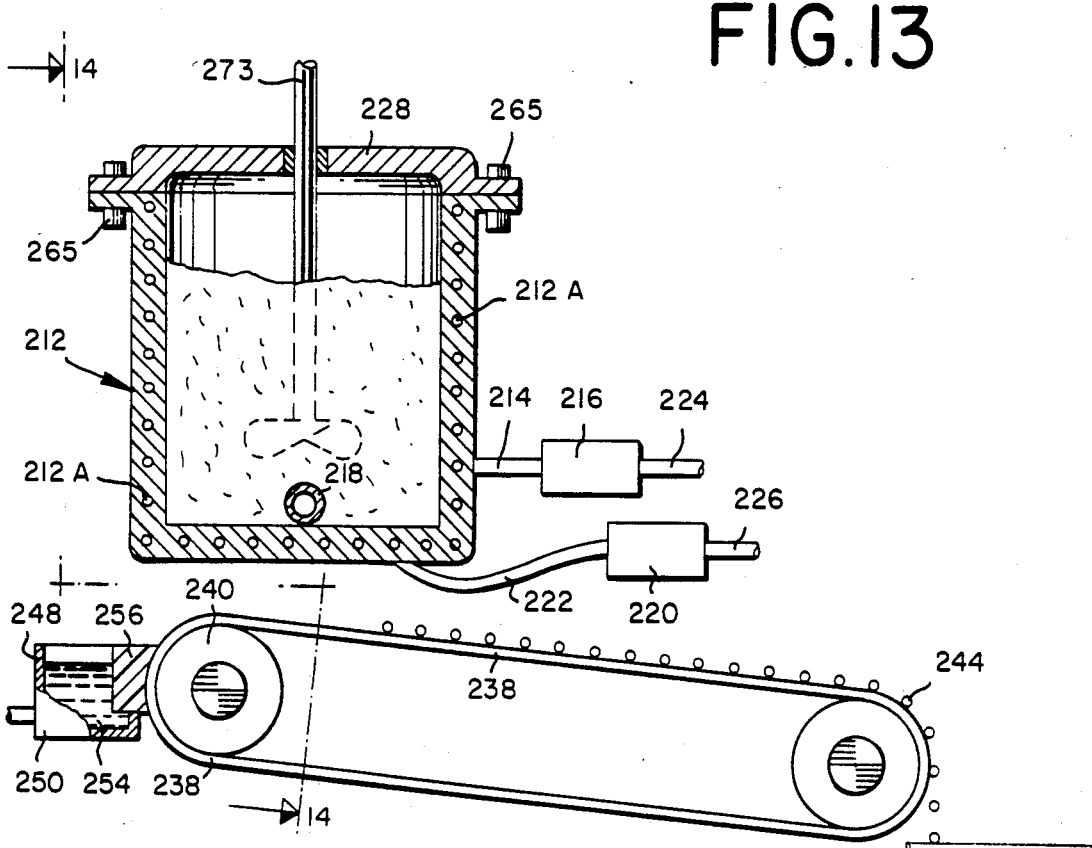

FIG. 13 is a partial side elevation and partial sectional view of an apparatus for forming polymer pellets centered with at least one of the norbornyl pyridine derivatives of our invention.

Figure 14:
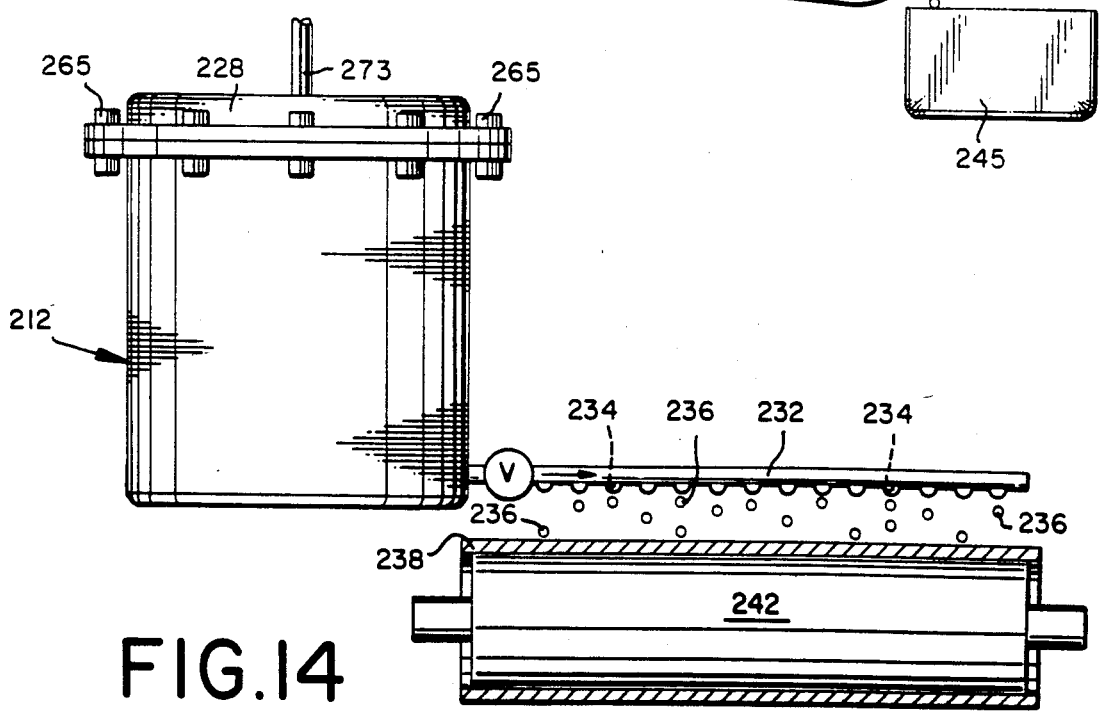

FIG. 14 is a section taken on the line 14—14 of FIG. 13.

DETAILED DESCRIPTION OF THE DRAWINGS

Referring to FIGS. 13 and 14 in particular, the apparatus used in producing polymeric fragrances containing the norbornyl pyridine derivatives of our invention comprises a device for forming scented polyolefin (for example) pellets which comprises a vat or container 2101 into which a mixture of polyolefin such as polyethylene and an aromatic substance or scented material is placed (in this case at least one of the norbornyl pyridine derivatives of our invention). The container is closed by an airtight lid 228 and clamped to the container by bolts 265. A stirrer 273 traverses the lid or cover 228 in airtight manner and is rotated in a suitable manner. A surrounding cylinder 212 having heating coils which are supplied with electric current through cable 224 from a rheostat or control 216 is operated to maintain a temperature inside the container 2101 such that polyethylene or other thermoplastic polymer in the container will be maintained in the molten or liquid state. It has been found advantageous to employ a colorless odorless polymer (e.g., polyethylene) with a viscosity ranging between 180 and 220 saybolt seconds and having a melting point in the range of 200°–280° F. The heater 2201 is operated to maintain the upper portion of the container 2101 within a temperature range of from 250°–350° F. The bottom portion of the container 218 is heated by means of heating coils 222 heated through a control 220 connected thereto through a connecting wire 226 to maintain a lower portion of the container 218 within a temperature range of from 250°–350° F.

Thus, polymer (e.g., polyethylene) is added to container 2101 and is heated from 10–12 hours whereafter a scented aroma imparting material (at least one of the norbornyl pyridine derivatives of our invention) is added quickly to the melt. The material must be compatible with polyolefin and forms a homogeneous liquid melt therewith. The scented material is of a type for the particular aroma desired and formulated specifically for the scenting purpose for which the polyolefin will be employed.

Generally, about 5–30% by weight of the scented material (at least one of the norbornyl pyridine derivatives of our invention) are added to the polyolefin.

After the scent imparting material (e.g., one of the norbornyl pyridine derivatives of our invention) is added to container 2101, the mixture is stirred for a few minutes for example, 5–15 minutes and maintained within the temperature range as indicated previously by the heating coils 212 and 218, respectively. The controls 216 and 220 are connected through cables 224 and 226 to a suitable power supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g., polyolefin) and aroma mixture will continuously drop through orifices 234 downwardly from the conduit 232. During this time, the temperature of the polymer (e.g., polyolefin) and aroma mixture in the container 2101 (e.g., one of the norbornyl pyridine derivatives of our invention) is accurately controlled so that a temperature in the range of from about 210°–275° F. will exist in the conduit 232. The regulation of the temperature through the control 216 and the control 2201 is essential in order to insure temperature balance to provide for the continuous dropping or dripping of molten polymer (e.g., polyethylene) and scenting material (e.g., one or more of the norbornyl pyridine derivatives of our invention) mixture through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238 they form pellets 244 which harden almost instantaneously and fall off the end of the conveyor 238 into a container 259 which is advantageously filled with water or some other suitable cooling liquid to insure the rapid cooling of each of the pellets. The pellets 244 are then collected from the container 259 and utilized in processes as illustrated infra.

A feature of this aspect of the process of our invention is the provision for moistening the conveyor belts 238 to insure rapid formation of the solid polymer (e.g., polyolefin scented pellets 244 without sticking to the belt. The belt 238 is advantageously of a material which will not normally stick to a melted plastic but a moistening means 248 insures a sufficiently cold temperature of the belt surface for adequate formation of the pellets 244. The moistening means comprises a container 259 which is continuously fed with water 252 to maintain a level 254 for moistening a sponge element 256 which bears against the exterior surface of the belt 238.

THE INVENTION

The invention comprises the novel product as well as novel processes according to which such products are manufactured, this specific embodiments of which are described hereinafter by way of example and in accordance with which it is now preferred to practice the invention.

Briefly, the present invention provides norbornyl pyridine derivatives defined according to the generic structure:

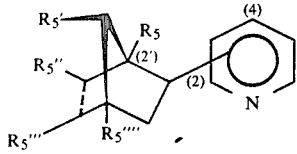

wherein the dashed line represents a carbon-carbon single bond or a carbon-carbon double bond and $R_5$, $R_5'$, $R_5''$, $R_5'''$ and $R_5''''$ each represents hydrogen or methyl with a proviso that at least four of $R_5$, $R_5'$, $R_5''$, $R_5'''$ and $R_5''''$ represent hydrogen; and wherein the bond joining the pyridinyl moiety with the norbornyl moiety at the 2' position of the norbornyl moiety is located at either the 2 position or the 4 position of the pyridine ring useful in augmenting or enhancing the aroma or taste of consumable materials including perfume compositions, colognes and perfumed articles; foodstuffs, chewing gums, toothpastes, medicinal products and chewing tobaccos.

The compounds defined according to the structure:

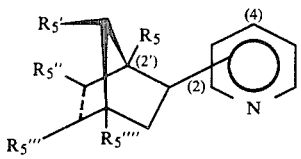

wherein the dashed line represents a carbon-carbon single bond or wherein the dashed line represents a carbon-carbon double bond and one of $R_5$, $R_5'$, $R_5''$, $R_5'''$ and $R_5''''$ is methyl are novel compounds.

The norbornyl pyridine derivatives of our invention augment or enhance the aroma of perfume compositions, colognes and perfumed articles by augmenting or enhancing petitgrain-like, neroli-like, verdima-like, green, herbaceous, galbanum-like, musk, amber, woody, rose, minty, cedarleaf, eucalyptus, bergamot, orris-like and balsamic-like with amber-like, woody, musk, rose, green, herbaceous, leafy, minty and vanoris-like undertones.

The norbornyl pyridine derivatives of our invention also augment or enhance bell pepper-like, green vegetable, galbanum-like, floral, pear-like, peach-like, orange-albedo, minty, cinnamon-like and bitter chocolate-like aroma and taste nuances in foodstuffs, chewing gums, toothpastes, medicinal products and chewing tobaccos.

Examples of the norbornyl pyridine derivatives of our invention and their organoleptic properties are set forth in the following Table I:

TABLE I

| NORBORNYL PYRIDINE DERIVATIVES OF OUR INVENTION | PERFUME PROPERTY | FLAVOR PROPERTY |
|---|---|---|
| Compound having the structure: 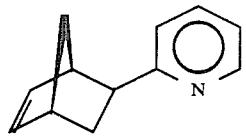 produced according to Example I. | A petitgrain-like, neroli-like, verdima-like, green, herbaceous, galbanum-like aroma with amber-like undertones. | A bell pepper, green vegetable, galbanum and floral-like aroma and taste profile at 0.1 ppm causing it to be useful in green vegetable and bell pepper flavors. |
| Compound having the structure: 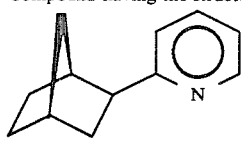 produced according to Example II. | A musk and amber aroma with woody undertones. | A pear-like, peach-like and walnut-like aroma and taste profile at 5 ppm. |
| Compound having the structure: 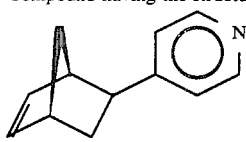 produced according to Example III | A woody aroma with musk, amber and rose undertones. | A pear-like, peach-like and walnut-like aroma and taste profile at 2 ppm. |
| Compound having the structure: 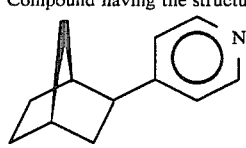 produced according to Example IV | A petitgrain and rose aroma profile with woody, musk and amber undertones. | An orange-albedo aroma and taste profile at 20 ppm causing it to be useful in fresh orange juice flavors. |

TABLE I-continued

NORBORNYL PYRIDINE DERIVATIVES OF OUR INVENTION

| NORBORNYL PYRIDINE DERIVATIVES OF OUR INVENTION | PERFUME PROPERTY | FLAVOR PROPERTY |
|---|---|---|
| Mixtures of compounds having the structure:<br>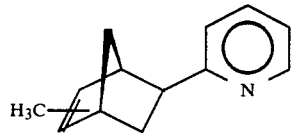<br>produced according to Example V | A green, herbaceous, minty, cedarleaf, eucalyptus and bergamot aroma with green, herbaceous, leafy and minty nuances on dry out. | A fresh natural green, natural orange-albedo character at 0.5 ppm. |
| Mixture of compounds defined according to the structure:<br>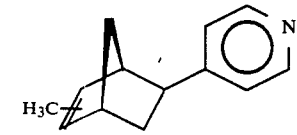<br>produced according to Example VI | A green, woody, cinnamon-like, orris-like and balsamic aroma profile with vanoris-like undertones. | A cinnamon and bitter chocolate aroma and taste profile at 0.1 ppm. |

The norbornyl pyridine derivatives of our invention are produced by reacting a vinyl pyridine defined according to the structure:

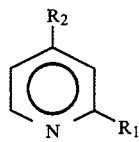

where one of $R_1$ or $R_2$ is vinyl and the other of $R_1$ or $R_2$ is hydrogen with bicyclopentadiene compound defined according to the structure:

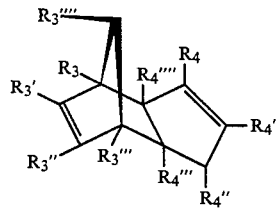

wherein $R_3$, $R_3'$, $R_3''$, $R_3'''$ and $R_3''''$ represent hydrogen or methyl with at least four of $R_3$, $R_3'$, $R_3''$, $R_3'''$ and $R_3''''$ being hydrogen and wherein $R_4$, $R_4'$, $R_4''$, $R_4'''$ and $R_4''''$ each represents methyl or hydrogen with at least four of $R_4$, $R_4'$, $R_4''$, $R_4'''$ and $R_4''''$ being hydrogen according to the reaction:

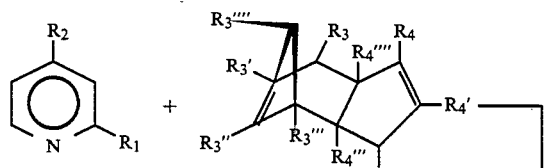

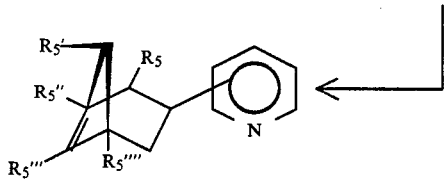

The resulting compound may be used "as-is" for its organoleptic properties or it may be further reacted with hydrogen using a hydrogenation catalyst according to the reaction:

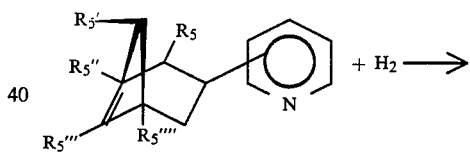

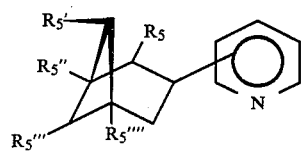

wherein $R_5$, $R_5'$, $R_5''$, $R_5'''$ and $R_5''''$ each represents hydrogen or methyl with at least four of $R_5$, $R_5'$, $R_5''$, $R_5'''$ and $R_5''''$ representing hydrogen.

More specifically, the reaction of the bicyclopentadiene moiety with the vinyl pyridine takes place at reflux conditions in the absence of solvent with a mole ratio of bicyclopentadiene derivative:vinyl pyridine derivative being approximately 1:1 with a slight excess of bicylopentadiene derivative. The reaction time may vary from about three hours up to about 15 hours; the reaction temperature may vary from about 140° C. up to about 180° C. with the reaction temperature being dependent upon the reactants employed and the pressure of reaction. It is most convenient and preferable to carry out the reaction at atmospheric pressures but pressures above atmospheric or below atmospheric may be utilized without substantially affecting the yield of reaction product. The reaction is preferably carried out in the presence of an Ionox ® catalyst. Ionox ® is p-t-butyl catechol.

At the end of the reaction, the reaction mass may be "worked up" using the standard procedures and subsequently distilled as by means of fractional distillation. The resulting product may be used "as-is" for its organoleptic properties or it may be further reacted with hydrogen. The reaction takes place in the presence of an inert solvent such as isopropyl alcohol at a temperature in the range of from about 25° C. up to about 100° C. and at a pressure in the range of from about 400 psig up to about 1500 psig. The reaction is necessarily carried out in a reactor that is equipped to withstand such pressures and temperatures. The reaction time may vary between about five hours and 20 hours, depending upon the yield of desired hydrogenated product. In certain instances it is useful to obtain a low yield of hydrogenated product and retain the mixture of hydrogenated and unhydrogenated derivative having the structures:

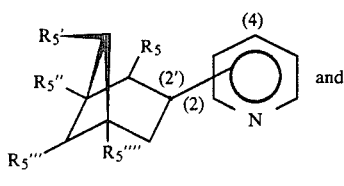

The proportion of hydrogenated to unhydrogenated derivative being determinative of the particular organoleptic properties sought in the resulting reaction product. The hydrogenation is carried out using standard hydrogenation techniques and a hydrogenation catalyst such as palladium-on-carbon (e.g., 5–15% palladium-on-carbon), palladium-on-calcium carbonate and Raney nickel.

The hydrogenation reaction:

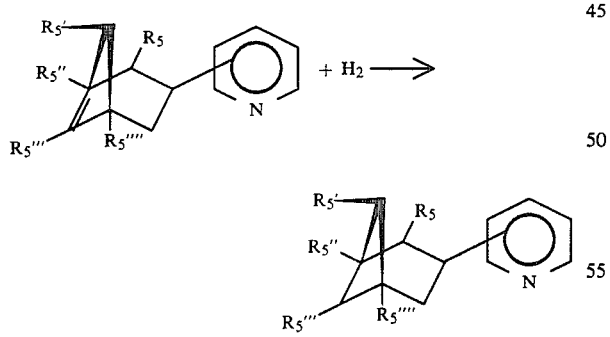

is carried out utilizing standard hydrogenation techniques and a hydrogenation catalyst such as palladium-on-carbon (e.g., 5–15% palladium-on-carbon) at temperatures of between 130°–170° C. and pressures of between 40 and 250 psig.

When the norbornyl pyridine derivatives of our invention are used as food flavor adjuvants, the nature of the co-ingredients included with the norbornyl pyridine derivatives used in formulating the product composition will also serve to alter, modify, augment or enhance the organoleptic characteristics of the ultimate foodstuff treated therewith.

As used herein, in regard to flavors, the terms "alter", "modify" and augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquid which are ingestible non-toxic materials which have medicinal value such as cough syrup, cough drops, aspirin and chewable medicinal tablets.

The term "chewing gum" is intended to mean a composition which comprises a substantially water-insoluble, chewable plastic gum base such a chickle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which includes one or more of the norbornyl pyridine derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may, in general, be characterized as flavoring ajuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), priopyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth, guar gum and xantan gum; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethylacrolein, methyl-n-amyl ketone, n-hexenal,2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-cotanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-2-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myrsitate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons, such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophylene, 1-phellandrene, p-cymene, 1-alphapinene; pyrazines, such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, 2-methoxy-3-isobutyl pyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones, such as δ-nonalctone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the norbornyl pyridine derivatives of our invention by not covering or spoiling the organoleptic properties (aroma and/or taste) thereof; (ii) be non-reactive with the norbornyl pyridine derivatives of our invention and (iii) be capable of providing an environment in which the norbornyl pyridine derivatives of our invention can be dispersed or admixed to provide a homogeneous medium.

In addition, selection of one or more flavoring adjuvants, as well as the quantities thereof, will depend upon the precise organoleptic character desired in the finished product. Thus, in the case of flavoring compositions, ingredient selection will vary in accordance with the foodstuff, chewing gum, medicinal product, toothpaste or chewing tobacco to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the norbornyl pyridine derivatives employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the norbornyl pyridine derivatives of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consitent with the obtention of desired flavoring effects.

Thus, and with respect to ultimate food compositions, chewing gum compositions, medicinal product compositions, chewing tobacco compositions, chewing gum compositions and toothpaste compositions, it is found that quantities of norbornyl pyridine derivatives ranging from a small but effective amount, e.g., 0.5 parts per million up to about 100 parts per million based on total composition are suitable. Concentrations in excess of the maximum quantity stated are not normally recommended, since they fail to provide commensurate enhancement of organoleptic properties. In those instances wherein the norbornyl pyridine derivatives of our invention are added to the foodstuff as an integral component of a flavoring composition, it is, of course, essential that the total quantity of flavoring composition employed be sufficient to yield an effective concentration of norbornyl pyridine derivatives in the foodstuff product.

Food flavoring compositions prepared in accordance with the present invention preferably contain the norbornyl pyridine derivatives in concentrations ranging from about 0.1% up to about 15% by weight based on the total weight of the said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the norbornyl pyridine derivatives of our invention with, for example, gum arabic, gum tragacanth, guar gum, xanthan gum, carrageenan and the like, and thereafter spray-drying the resultant mixture whereby to obtain the particulate solid product. Preprepared flavor mixes in powder form, e.g., a fruit-flavored powder mix, are obtained by mixing the dried solid components, e.g., starch, sugar and the like and one or more of the norbornyl pyridine derivatives of our invention in a dry blender until the requisite degree of uniformity is achieved.

It is presently preferred to combine with the norbornyl pyridine derivatives of our invention, the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
$\beta$-Damascone(1-crotonyl-2,2,6-trimethylcyclohex-1-ene);
$\beta$-Damascenone(1-crotonyl-2,2,6-trimethylcyclohex-1-ene);
Beta-cyclohomocitral(2,2,6-trimethylcyclohex-1-ene carboxaldehyde;
Isoamyl butyrate;
Cis-3-hexenol-1;
2-Methyl-2-pentneoic acid;
Elemecine(4-allyl-1,2,6-trimethoxybenzene);
Isoelemecine(4-propenyl-1,2,6-trimethoxybenzene);
2-(4-Hydorxy-4-methylpentyl)norbornadiene;
2-Methoxy-3 isobutyl pyrazine;
Methylmercaptan;
$\beta$-Ionone;
2,4-Decadienal;
2,6-cis-Nonadienal;
Ethyl-2-methylbutyrate;
Amyl acetate; and
Benzaldehyde.

The norbornyl pyridine derivatives of our invention and one or more auxiliary perfume ingredients, including for example, alcohols, aldehydes, ketones, terpinic hydrocarbons, nitriles, esters, amines other than the norbornyl pyridine derivatives of our invention, natural synthetic oils and synthetic essential oils may be admixed so that the combined odors of the individual components produce a pleasant and desired fragrance, particularly and preferably in the floral, musk, woody, rose, herbaceous and minty and orris fragrances.

Such perfume compositions usually contain (a) the main note or the "bouquet" or foundation stone of the composition; (b) modifiers which round off and accompany the main note; (c) fixatives which include odorous compositions which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, the norbornyl pyridine derivatives of our invention can be used to alter, modify or enhance the aroma characteristics of a perfume composition, for example, by utilizing or moderating the olfactory reaction contributed by another ingredient in the composition.

The amount of the norbornyl pyridine derivatives of our invention which will be effective in perfume compositions as well as in perfumed articles and colognes depends on many factors, including the other ingredients, their amounts and the effects which are desired. It has been found that perfume compositions containing as little as 0.01% of the norbornyl pyridine derivatives of our invention or even less (e.g., 0.005%) can be used to impart, augment or enhance petitgrain-like, neroli-like, verdima-like, green, herbaceous, galbanum-like, musk, amber, woody, rose, minty, cedarleaf, eucalyptus, bergamot, cinnamon-like, orris-like, and balsamic-like with amber-like, woody, musk, rose, green, herbaceous, leafy, minty and vanoris-like undertones to soaps, cosmetics or other products. The amount employed can range up to 70% of the fragrance components and will depend on consideration of cost, nature of the end product, the effect desired on the finished product and the particular fragrance sought.

The norbornyl pyridine derivatives of our invention are useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and the like. When used as (an) olfactory component(s) in perfumed articles as little as 0.1% of the norbornyl pyridine derivatives of our invention or composition containing a high proportion of the norbornyl pyridine derivatives of our invention will suffice to impart, augment or enhance intense long lasting petitgrain-like, neroli-like, verdima-like, green, herbaceous, galbanum-like, musk, amber, woody, rose, minty, cedarleaf, eucalyptus, bergamot, cinnamon-like, orris-like, and balsamic aromas with amber-like woody, rose, musk, rose, green, herbaceous, leafy, minty and vanoris-like undertones.

The range of norbornyl pyridine derivatives of our invention useful in perfumed articles including solid or liquid anionic, cationic, nonionic and zwitterionic detergents, soaps, space odorants and deodorants, bath preparations, such as creams, deodorants, hand lotions and sun screens; powders, such as talcs, dusting powders, face powders and the like and perfumed polymers may vary from as little as 0.1% to as much as 5% of the norbornyl pyridine derivatives of our invention.

In addition, the perfume composition or fragrance composition of our invention can contain a vehicle or carrier for the norbornyl pyridine derivatives or composition containing norbornyl pyridine derivatives of our invention. The vehicle can be a liquid, such as an alcohol, such as ethyl alcohol, a non-toxic glycol, such as propylene glycol or the like. The carrier can also be an absorbent solid, such as gum (i.e., gum arabic, guar gum, xanthan gum or the like) or components for encapsulating the composition (such as gelatin when encapsulation is carried out by means of coacervation or such as a urea formaldehyde prepolymer when encapsulation is carried out by forming a polymeric wall around a liquid perfume scenter).

It is well known in the tobacco art that the domestic tobaccos which are exemplified by burley, Maryland, flue-cured, bright leaf or Virginia tobaccos are low in flavor as compared with so-called oriental or aromatic tobaccos which are imported from Turkey, Greece, Bulgaria, Yugoslavia, Rhodesia, and Russia. Accordingly, it has been common practice in the tobacco industry to prepare blends of domestic and oriental tobaccos in order to provide cigarettes which have desired flavor and aroma characteristics. This invention also provides a tobacco which has an enhanced flavor and aroma.

With reference to this aspect of our invention which concerns tobacco flavoring, the norbornyl pyridine derivatives of our invention are added to tobacco in amounts to provide generally a tobacco in which is dispersed about 0.00005 to about 0.3 percent by weight of the additive. Preferably, the amount of additive is between about 0.0003 and about 0.2 percent by weight in order to provide tobacco having a desired flavor and aroma. The preferred percentages may be somewhat less, however, if other flavorants imparting a desired aroma are also employed. The additives may be applied in any suitable manner and preferably in the form of a liquid solution or suspension by spraying, dipping or otherwise. The additives may be incorporated at any step in the treatment of tobacco, but are preferably added after aging; curing and shredding and before the tobacco is formed into tobacco products such as cigarettes, cigars and the like. Likewise, it will be apparent that only a portion of the tobacco need be treated and the thus treated tobacco may be blended with other tobacco before the tobacco products are formed. In such cases, the tobacco treated may have the additives, in excess of the amounts above indicated so that when blended with other tobaccos the final product will have the percentage within the indicated range.

In accordance with one example of this invention, an aged, cured and shredded domestic burley tobacco is sprayed with a one percent ethyl alcohol solution of a mixture of compounds defined according to the structure:

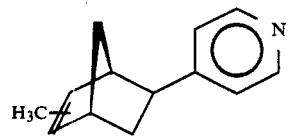

(produced according to Example VI, infra) in an amount to provide a tobacco composition containing a 0.005 percent by weight of the norbornyl pyridine derivatives of our invention on a dry basis. Thereafter, the alcohol is removed by evaporation and the tobacco is manufactured into cigarettes by the usual techniques. The cigarette, when treated as indicated, has a desired and pleasing aroma which is detectable in the main and side smoke streams when the cigarette is smoked; this aroma is described by some smokers as a woody cigar box-like note with pleasant cinnamon and oriental-like nuances in the after-taste.

It will be particularly apparent that the manner in which the norbornyl pyridine derivatives of our invention are applied to the tobacco is not particularly important since, as indicated it may be done in the form of spraying or dipping, utilizing suitable suspensions or solutions of the additive.

Thus, water or volatile organic solvents, such as alcohol, ether, acetone, volatile hydrocarbons and the like, may be used as the carrying medium for the additive while it is being applied to the tobacco. Also, other flavor and aroma producing additives, such as those disclosed in Jones, U.S. Pat. No. 2,766,145, the specification of which is incorporated by reference herein, and Schumacher, U.S. Pat. No. 2,978,365, the specification of which is incorporated by reference herein, may be incorporated into the tobacco with the additives of this invention.

While this invention is useful in the manufacture of cigarette tobacco, it is also suitable for use in connection with the manufacture of pipe tobacco, cigars and other tobacco products formed from sheeted tobacco dust or fines which are well known to the art. Likewise, the additives of the invention can be incorporated with materials such as filter tip materials, seam paste, packaging materials and the like which are used along with the tobacco to form a product adapted for smoking. Furthermore, the compounds can be added to certain tobacco substitutes of natural or synthetic origin and by the term "tobacco" as used throughout this specification is meant any composition intended for human consumption by smoking or otherwise, whether composed of tobacco plant parts, substitute materials or both.

The following Examples I–VI serve to illustrate methods for preparation of the norbornyl pyridine derivatives of our invention. The following Examples VII et seq show methods for utilizing the organoleptic properties of the norbornyl pyridine derivatives of our invention. It will be understood that these examples are illustrative and the invention is to be considered as restricted thereto only as indicated in the appended claims.

EXAMPLE I

Preparation of Vinyl Pyridine Dicyclopentadiene Adduct

Reaction:

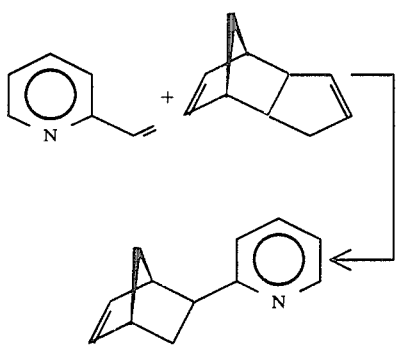

Into a 2 liter reaction vessel equipped with stirrer thermometer, reflux condenser and thermometer are placed the following materials:

500 grams vinyl pyridine (4.76 moles)
660 grams dicyclopentadiene (5.0 moles)
10 grams Ionox ®

With stirring, the mixture is heated to reflux (147°–158° C.) and refluxed for a period of eight hours. At the end of the reaction, the reaction mass is charged to a splash column packed with saddles and distilled yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 38/43 | 76/110 | 5/3 | 118 |
| 2 | 87 | 109 | 3.0 | 41 |
| 3 | 95 | 114 | 3.5 | 88 |
| 4 | 101 | 140 | 3.5 | 262 |
| 5 | 125 | 170 | 3.0 | 90 |
| 6 | 165 | 210 | 2.0 | 219 |
| 7 | 130 | 210 | 2.0 | 31 |

Fractions 2–6 are bulked and redistilled on a 12″ Goodloe column yielding the following fractions:

| Fraction No. | Vapor Temp. (°C.) | Liquid Temp. (°C.) | Vacuum mm/Hg. Pressure | Weight of Fractions (gms) |
|---|---|---|---|---|
| 1 | 77/86 | 105/110 | 2.5 | 22 |
| 2 | 86 | 106 | 2.2 | 22 |
| 3 | 90 | 108 | 2.2 | 21 |
| 4 | 87 | 107 | 2.2 | 26 |
| 5 | 88 | 108 | 2.2 | 17 |
| 6 | 91 | 109 | 2.2 | 27 |
| 7 | 88 | 108 | 2.2 | 13 |
| 8 | 89/89 | 112/110 | 2.6 | 20 |
| 9 | 86 | 110 | 2.6 | 22 |
| 10 | 85 | 111 | 1.8 | 23 |
| 11 | 86 | 113 | 1.8 | 28 |
| 12 | 86 | 118 | 1.8 | 22 |
| 13 | 92 | 126 | 1.8 | 21 |
| 14 | 92 | 126 | 1.8 | 15 |

Bulked fractions 2–12 (exo:endo ratio 55:45) has a petit-grain, neroli-like, verdima-like, green, herbaceous, and galbanum aroma with petitgrain-like, green, ambrett-seed undertones.

Figure 1:
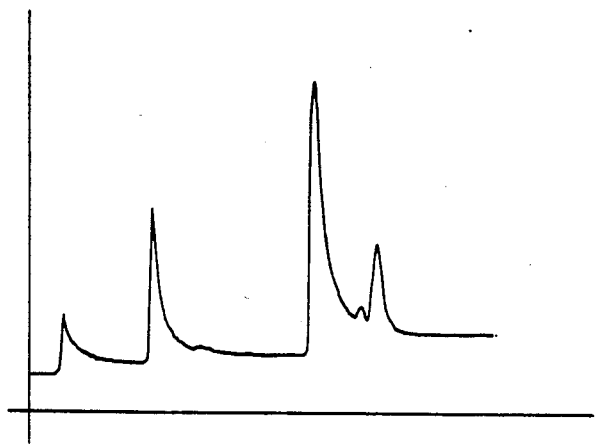
FIG. 1 is the GLC profile for the crude reaction product of Example I containing the compound having the structure.

FIG. 1 is the GLC profile for the crude reaction product prior to distillation (Conditions: SE-30 column programmed at 100°–220° C. at 8° C. per minute).

FIG. 2 is the NMR spectrum for the resulting distillation product (Conditions: Field strength: 100 MHz; solvent: CFCl₃).

The resulting distillation product also has an excellent green bell pepper, green vegetable, galbanum-like aroma and taste at 0.1 ppm causing it to be useful in green vegetable, bell pepper and salad dressing flavors.

EXAMPLE II

Preparation of 2-(2-Norbornyl)Pyridine

Reaction:

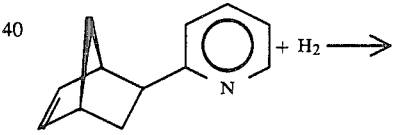

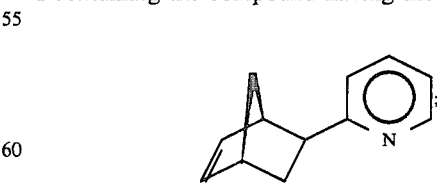

Into a 1 liter autoclave equipped for high pressure is placed 230 grams of the distillation product of Example I containing the compound having the structure:

230 grams of isopropyl alcohol and 7 grams of Raney nickel. The autoclave is sealed and heated to 80° C. at 600 psig pressure, the pressure being supplied with hydrogen. Th autoclave is maintained at 600 psig and 80° C. for a period of five hours. At the end of the five hour period, the autoclave is opened and the reaction mass is filtered and distilled on a splash column packed with saddles yielding the following fractions:

| Faction No. | Vapor Temp. (°C.) | Liquid Temp. (°C.) | Vacuum mm/Hg. Pressure |
|---|---|---|---|
| 1 | 41 | 44 | 200 |
| 2 | 35 | 102 | 1 |
| 3 | 84/ | 104/ | 1 |

Bulked fractions 1-3 of the resulting product has a musk, amber aroma with woody undertones. From a flavor standpoint, the resulting product has a pear-like, peach-like and walnut-like aroma and taste profile at 5 ppm.

FIG. 3 is the GLC profile of the crude reaction product (Conditions: Carbowax column programmed at 100°-200° C. at 8° C. per minute).

FIG. 4 is the NMR spectrum for fraction 1 of the above-mentioned distillation (Conditions: Field strength: 100 MHz; solvent: CFCl₃).

EXAMPLE III

Preparation of 4-Vinyl Pyridine Bicyclopentadiene Adduct

Reaction:

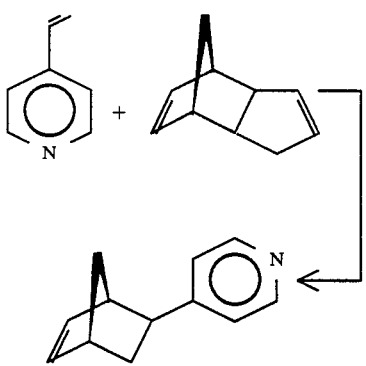

Into a 2 liter reaction vessel equipped with reflux condenser, thermometer, heating mantle and stirrer is placed the following materials:

500 grams 4-vinyl pyridine (4.76 moles)
660 grams bicyclopentadiene (5.0 moles)
10 grams Ionox ®

The resulting mixture is heated to reflux at a temperature of 154°-156° C. for a period of nine hours. At the end of the nine hour reaction period, the reaction mass is distilled using a splash column packed with saddles yielding the following fractions:

| Faction No. | Vapor Temp. (°C.) | Liquid Temp. (°C.) | Vacuum mm/Hg. Pressure | Weight of Fraction (gms) |
|---|---|---|---|---|
| 1 | 60/54 | 91/122 | 16/10 | 261 |
| 2 | 104 | 120 | 3 | 40 |
| 3 | 107 | 128 | 3 | 89 |
| 4 | 108 | 130 | 3 | 166 |
| 5 | 112 | 132 | 3 | 240 |
| 6 | 120 | 162 | 3 | 215 |
| 7 | 170 | 200 | 3 | 35 |

Fractions 2-7 are bulked and redistilled on a 12" Goodloe column yielding the following fractions:

| Faction No. | Vapor Temp. (°C.) | Liquid Temp. (°C.) | Vacuum mm/Hg. Pressure | Weight of Fraction (gms) |
|---|---|---|---|---|
| 1 | 96/101 | 118/118 | 1.8 | 23 |
| 2 | 103 | 119 | 1.8 | 22 |
| 3 | 103 | 119 | 1.8 | 22 |
| 4 | 105 | 119 | 1.8 | 61 |
| 5 | 107 | 121 | 1.8 | 42 |
| 6 | 107 | 121 | 1.8 | 46 |
| 7 | 107 | 121 | 1.8 | 55 |
| 8 | 108 | 123 | 1.8 | 42 |
| 9 | 108 | 123 | 1.8 | 64 |
| 10 | 108 | 123 | 1.8 | 64 |
| 11 | 108 | 123 | 1.8 | 43 |
| 12 | 105 | 120 | 1.6 | 45 |
| 13 | 105 | 143 | 1.6 | 29 |
| 14 | 105 | 150 | 1.6 | 23 |
| 15 | 105 | 180 | 1.6 | 54 |
| 16 | 100 | 215 | 1.6 | 23 |

FIG. 5 is the GLC profile for the crude reaction product (Conditions: SE-30 column programmed at 100°-220° C. at 8° C. per minute).

FIG. 6 is the NMR spectrum for fraction 6 of the foregoing distillation (Conditions: Field strength: 100 MHz; solvent: CFCl₃).

The resulting product has an excellent woody aroma with musk, amber and rose undertones. From a flavor standpoint it has an excellent pear, peach and walnut-like aroma and taste profile at 2 ppm.

EXAMPLE IV

Preparation of 4-(2-Norbornyl)Pyridine

Reaction:

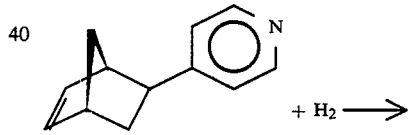

+ H₂ ⟶

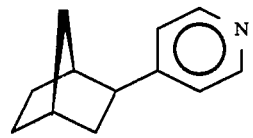

Into a 1 liter autoclave equipped for high pressure is placed 300 grams of the reaction product of Example III (1.75 moles) having the structure:

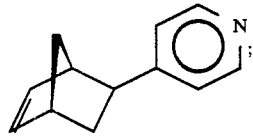

300 grams of anhydrous isopropyl alcohol and 6 grams of Raney nickel.

The autoclave is sealed and heated to 30°-38° C. while simultaneously being pressurized with hydrogen to 300 psig. The pressurization with hydrogen is maintained at 300 psig and the temperature is maintained at 38°–39° C. for a period of eight hours. At the end of the eight hour period the autoclave is cooled and opened. The contents are filtered and the resulting product is stripped of solvent and then distilled on a splash column packed with saddles, yielding the following fractions:

| Faction No. | Vapor Temp. (°C.) | Liquid Temp. (°C.) | Vacuum mm/Hg. Pressure | Weight of Fraction (gms) |
|---|---|---|---|---|
| 1 | 50/53 | 55/90 | 300 | — |
| 2 | 23 | 91 | 3 | — |
| 3 | 100/105 | 118/166 | 1/ | 299 |
| 4 | 92 | 200 | 600 | — |

The resulting product has an excellent petitgrain aroma with rose, woody, musk and amber undertones. From a flavor standpoint, the resulting product has an excellent orange-albedo flavor at 20 ppm.

FIG. 7 is the GLC profile for the crude reaction product prior to distillation (Conditions: Carbowax column programmed at 100°–220° C. at 8° C. per minute).

FIG. 8 is the NMR spectrum for the foregoing distillation product (Conditions: Field strength: 100 MHz; solvent: CFCl₃).

EXAMPLE V

Preparation of 2-Vinylpyridine-Methylcyclopentadiene Adduct

Reaction:

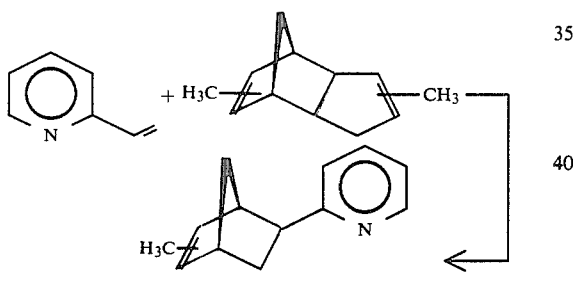

Into a 2 liter reaction flask equipped with stirrer, reflux condenser, thermometer and heating mantle are placed:
- 333 grams 2-vinylpyridine (2.17 moles)
- 673 grams methylcyclopentadiene (95%) (4.0 moles)
- 5 grams Ionox ®

The resulting mixture is heated to reflux (163°–173° C.) and maintained at reflux for a period of eight hours. The resultant product, 1019 grams of crude, is charged to a still and rushed over. The rushed-over product is then fractionally distilled on a 12" Goodloe column yielding the following fractions:

| Faction No. | Vapor Temp. (°C.) | Liquid Temp. (°C.) | Vacuum mm/Hg. Pressure | Weight of Fraction (gms) |
|---|---|---|---|---|
| 1 | 46/56 | 115/115 | 2.2 | 22 |
| 2 | 84 | 116 | 1.8 | 28 |
| 3 | 98 | 123 | 2.6 | 37 |
| 4 | 105 | 120 | 3.4 | 40 |
| 5 | 99 | 123 | 2.6 | 41 |
| 6 | 97 | 125 | 2.4 | 51 |
| 7 | 97 | 126 | 2.4 | 57 |
| 8 | 97 | 128 | 2.4 | 49 |
| 9 | 98 | 130 | 2.4 | 54 |
| 10 | 98 | 145 | 2.4 | 49 |
| 11 | 102 | 165 | 2.4 | 20 |
| 12 | 100 | 220 | 2.4 | 11 |

Fractions 5–8 are bulked and the bulked product is evaluated for its organoleptic properties.

FIG. 9 is the GLC profile of the crude reaction product (Conditions: SE-30 column programmed at 100°–220° C. at 8° C. per minute).

FIG. 10 is the NMR spectrum for the resulting distillation product (Conditions: Field strength: 100 MHz; solvent: CFCl₃). The resultant product has an excellent herbaceous, minty, green, cedarleaf-like, eucalyptus-like, citrus (bergamot) aroma profile with green, herbaceous, leafy and minty undertones. The resultant product has a fresh natural green minty aroma and taste at 0.5 ppm from a food flavor standpoint.

EXAMPLE VI

Preparation of 4-Vinylpyridine-Methylcyclopentadiene Adduct

Reaction:

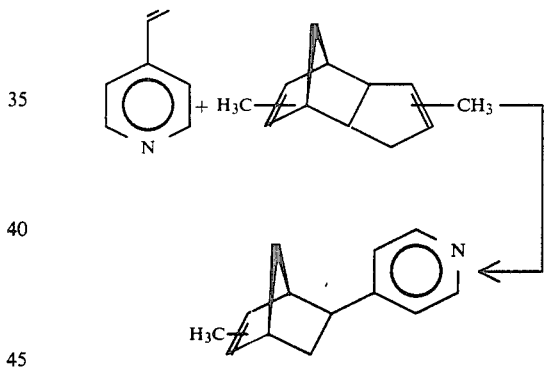

Into a 3 liter reaction vessel equipped with stirrer, thermometer, reflux condenser and heating mantle is placed the following materials:
- 893 grams 4-vinylpyridine (8.50 moles)
- 1500 grams methylcyclopentadiene (95%) (8.9 moles)
- 10 grams Ionox ®

The resulting mixture is heated to reflux and refluxed at 173° C.–180° C. over a period of eight hours. At the end of the eight hour period, the reaction mass was cooled and placed into a short path distillation column. The resulting product is rushed over and fractions 3–5 are bulked and redistilled on a 12" Goodloe column yielding the following fractions:

| Fraction No. | Vapor Temp. (°C.) | Liquid Temp. (°C.) | Vacuum mm/Hg. Pressure | Reflux Ratio R/D | Weight of Fraction (gms) |
|---|---|---|---|---|---|
| 1 | 35/68 | 106/111 | 1.2 | 9:1 | 16 |
| 2 | 88 | 120 | 1.0 | 9:1 | 19 |
| 3 | 92 | 121 | 1.0 | 8:2 | 47 |
| 4 | 92 | 121 | 1.0 | 8:2 | 61 |
| 5 | 92 | 121 | 1.0 | 8:2 | 60 |

-continued

| Fraction No. | Vapor Temp. (°C.) | Liquid Temp. (°C.) | Vacuum mm/Hg. Pressure | Reflux Ratio R/D | Weight of Fraction (gms) |
|---|---|---|---|---|---|
| 6 | 89/97 | 121/128 | 1.2 | 1:1 | 42 |
| 7 | 93 | 124 | 1.0 | 1:1 | 44 |
| 8 | 95 | 127 | 1.0 | 1:1 | 49 |
| 9 | 105 | 131 | 1.6 | 1:1 | 61 |
| 10 | 95 | 128 | 1.1 | 1:1 | 28 |
| 11 | 95 | 128 | 1.1 | 1:1 | 48 |
| 12 | 95 | 130 | 1.0 | 1:1 | 10 |
| 13 | 96 | 135 | 1.0 | 1:1 | 43 |
| 14 | 92 | 150 | 1.1 | 1:1 | 48 |
| 15 | 92/138 | 165/210 | 1.1 | 1:1 | 46 |

FIG. 11 is the GLC profile for the crude reaction product prior to distillation (Conditions: SE-30 column programmed at 100°–220° C. at 8° C. per minute).

FIG. 12 is the NMR spectrum for fraction 5 of the foregoing distillation containing a mixture of compounds defined according to the structure:

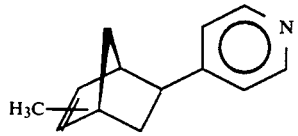

(Conditions: Field strength: 100 MHz; solvent: CFCl$_3$).

The resulting product has a green, woody, cinnamon-like, orris-like and balsamic aroma with vanoris undertones. From a flavor standpoint, it has a cinnamon bitter chocolate aroma and taste profile at 0.1 ppm.

EXAMPLE VII

The following composition is prepared (parts by weight):

| Ingredient | Parts by Weight |
|---|---|
| Bergamot oil | 120 |
| Methyl ionone | 60 |
| Jasmin extra | 80 |
| Petitgrain | 60 |
| Patchouli oil | 60 |
| Violet perfume base | 60 |
| Compound having the structure: | 20 |

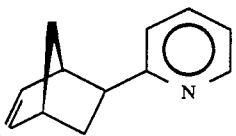

produced according to Example I

| Lemon oil | 80 |
|---|---|
| Rose Geranium oil | 120 |
| Lavender oil, French | 120 |
| Sweet Orange Oil | 80 |
| Musk extract, 3% | 50 |
| Civet extract, 3% | 50 |
| | 960 |

The addition of the compound having the structure:

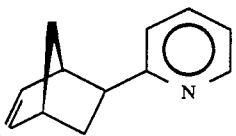

prepared according to Example I improves the overall quality of instant formulation lending a more petitgrain-like, neroli oil-like, verdima and galbanum effect thereto. Overall, the formulation can be described as bergamot with petitgrain, neroli, verdima, green, herbaceous and galbanum topnotes and amber undertones.

EXAMPLE VIII

The following composition is prepared:

| Ingredient | Parts by Weight |
|---|---|
| Linalyl acetate | 135.0 |
| Bergamot oil | 275.0 |
| Citronellol | 135.0 |
| Lavandulol | 135.0 |
| Portugal oil | 135.0 |
| Neroli oil | 40.5 |
| Jasmin oil | 20.5 |
| Jasmin absolute | 20.5 |
| Neroliol, Bigarade | 28.0 |
| Rosemary oil | 28.0 |
| Mixture of compounds defined according to the structure: | 28.5 |

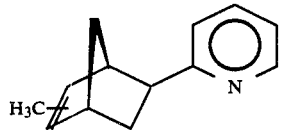

| prepared according to Example V | |
|---|---|
| Rose absolute | 13.5 |
| Hydroxy citronellol | 13.5 |
| Cyclopentadecanolide (10% in diethyl phthalate) | 7.0 |

The addition of the mixture of compounds defined according to the structure:

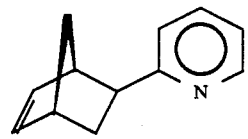

prepared according to Example V in the quantity given adds a distinct green, herbaceous, minty, cedarleaf-like, eucalyptus-like aroma to this fragrance. In the instant example the 20.5 parts of neroli oil can be replaced by 5 parts of the compound having the structure:

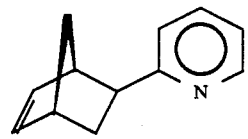

of this invention without changing the olfactory nature or quality of the fragrance. Overall the fragrance can be described as natural orange oil-like with green, herbaceous, minty, cedarleaf, eucalyptus-like and bergamot-like topnotes and green, herbaceous, leafy and minty undertones.

EXAMPLE IX

Perfume compositions are prepared with the following ingredients:

| Ingredients | IX(A) Parts By Weight | IX(B) Parts By Weight | IX(C) Parts By Weight |
|---|---|---|---|
| Vetivert oil | 40 | 40 | 40 |
| Sandalwood oil | 100 | 100 | 100 |
| Rose geranium oil | 200 | 200 | 200 |
| Musk extract (3% diethyl phthalate) | 25 | 25 | 25 |
| Civet extract (3% diethyl phthalate) | 25 | 25 | 25 |
| Benzyl-isoeugenol | 100 | 100 | 100 |
| Coumarin | 100 | 100 | 100 |
| Heliotropin | 50 | 50 | 50 |
| Bois de rose oil | 200 | 200 | 200 |
| Benzoin resin | 100 | 100 | 100 |
| Compound having the structure: produced according to Example II | 30 | 0 | 0 |
| Compound having the structure: produced according to Example III | 0 | 30 | 0 |
| Compound having the structure: produced according to Example IV | 0 | 0 | 30 |

A perfume composition exhibiting an excellent musk, amber and woody fragrance is produced when using the formulation of Example IX(A). When the compound having the structure:

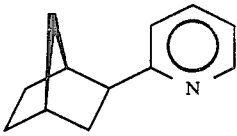

produced according to Example II is omitted the composition lacks the woody, amber fullness of the complete perfume composition of this example. The perfume composition of Example IX(A) can be described as having an intense woody, musky, amber aroma.

The perfume composition of Example IX(B) exhibits an excellent woody, musk, amber, rose aroma. When the compound having the structure:

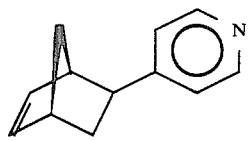

produced according to Example III is omitted the composition lacks the woody, amber fullness of the complete perfume composition of this Example. The perfume composition of Example IX(B) can be described as having an intense, long lasting woody, musk, amber, rose aroma.

The perfume composition of Example IX(C) exhibits an excellent petitgrain, rose, woody, musk, amber fragrance. When the compound having the structure:

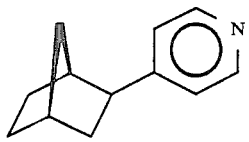

produced according to Example IV, is omitted, the composition lacks the woody amber fullness of the complete perfume composition of Example IX(C). The composition of Example IX(C) can be described as having a petitgrain, rose, woody, musk, amber fragrance.

EXAMPLE X

The following composition is prepared:

| Ingredients | Parts by Weight |
|---|---|
| Linalyl acetate | 135.0 |
| Bergamot oil | 275.0 |
| Citronellol | 135.0 |
| Lavandulol | 135.0 |
| Portugal oil | 135.0 |
| Neroli oil | 40.5 |
| Jasmin oil | 20.5 |
| Jasmin absolute | 20.5 |
| Neroliol, Bigarade | 28.0 |
| Rosemary oil | 28.0 |
| Mixture of compounds defined according to the structure: produced according to Example VI | 23.5 |
| Rose absolute | 13.5 |
| Hydroxy citronellol | 13.5 |
| Cyclopentadecanolide 10% | 7.0 |

The addition of the mixture of compounds defined according to the structure:

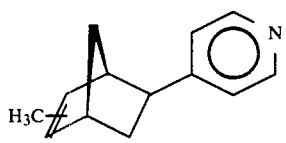

produced according to Example VI in the quantity given adds an excellent distinctive green, woody, cinnamon-like, orris-like, balsamic aroma to the fragrance. The fragrance can thus be described as balsamic with green, woody, cinnamon-like and orris-like topnotes and vanoris undertones.

EXAMPLE XI

Preparation of a Cosmetic Powder Composition

A cosmetic powder is prepared by mixing in a ball mill, 100 grams of talcum powder with 0.25 grams of one of the perfumery substances set forth in Table II below. Each of the cosmetic powders has an excellent intense aroma as set forth in Table II below:

TABLE II

| Perfume Substance | Perfumery Evaluation |
|---|---|
| Compound having the structure: [norbornene-pyridine] produced according to Example I | A petitgrain-like, neroli-like, verdima-like, green, herbaceous, galbanum-like aroma with amber-like undertones. |
| Compound having the structure: [norbornane-pyridine] produced according to Example II | A musk amber aroma with woody undertones. |
| Compound having the structure: [norbornene-pyridine] produced according to Example III | A woody aroma with musk, amber and rose undertones. |
| Compound having the structure: [norbornane-pyridine] produced according to Example IV | A petitgrain and rose aroma with woody, musk and amber undertones. |
| Mixture of compounds having the structure: [methyl-norbornene-pyridine] | A green, herbaceous, minty, cedar leaf-like, eucalyptus-like and bergamot-like aroma with green, herbaceous, leafy and minty nuances on dry out. |

TABLE II-continued

| Perfume Substance | Perfumery Evaluation |
|---|---|
| produced according to Example V Mixture of compounds having the structure: [methyl-norbornane-pyridine] produced according to Example VI | A green, woody, cinnamon-like, orris-like and balsamic aroma with van-oris-like undertones. |
| Perfume composition of Example VII | A bergamot with petitgrain, neroli, verdima, green, herbaceous, and galbanum topnotes and amber undertones. |
| Perfume composition of Example VIII | A natural orange oil-like with green, herbaceous, minty, cedar leaf, eucalyptus-like and bergamot-like topnotes and green, herbaceous, leafy and minty undertones. |
| Perfume composition of Example IX(A) | An intense woody, musk, amber aroma. |
| Perfume composition of Example IX(B) | An intense, long lasting woody, musk, amber, rose aroma. |
| Perfume composition of Example IX(C) | A petitgrain, rose, woody, musk, amber fragrance. |
| Perfume composition of Example X | A balsamic with green, woody, cinnamon-like, orris-like topnotes and vanoris undertones. |

EXAMPLE XII

Perfumed Liquid Detergent

Concentrated liquid detergents with aromas as set forth in Table II of Example XI (which detergents are prepared from Lysine salt of n-dodecyl benzene sulfonic acid as more specifically described in U.S. Pat. No. 3,948,818 issued on Apr. 6, 1976, the specification for which is incorporated by reference herein), are prepared containing each of the substances set forth in Table II of Example XI, supra. They are prepared by adding and homogeneously mixing the appropriate quantity of perfumery substance as set forth in Table II of Example XI in the liquid detergent. The detergents all possess aromas as set forth in Table II of Example XI, the intensity increasing with greater concentrations of perfumery substance of Table II of Example XI, supra.

EXAMPLE XIII

Preparation of a Cologne and Handkerchief Perfume

The perfume substances of Table II of Example XI, supra, are incorporated into colognes at concentrations of 1.5%, 2.0%, 2.5%, 3.0% and 4.0% in 80%, 85% and 90% aqueous ethanols; and into handkerchief perfume compositions at concentrations of 10%, 15%, 20%, 25%, and 30% (in 85%, 90% and 95% aqueous ethanols). Distinct and definitive aromas as set forth in Table II of Example XI are imparted to the cologne and to the handkerchief perfume compositions.

EXAMPLE XIV

Preparation of a Detergent Composition

A total of a 100 grams of a detergent powder (a nonionic detergent powder containing a proteo lytic enzyme prepared according to Example I of Canadian Letters Pat. No. 985,190 issued on Mar. 9, 1976, the disclosure of which is incorporated by reference herein), is mixed with 0.15 grams of each of the substances set forth in Table II of Example XI, supra, until substantially homogeneous compositions are obtained. These compositions have excellent aromas as set forth in Table II of Example XI.

EXAMPLE XV

Preparation of Soap

Each of the perfumery substances of Table II of Example XI are incorporated into soap (LVU-1) at 0.1% by weight of each substance. After two weeks in the oven at 90° F. each of the soaps showed no visual effect from the heat. Each of the soaps manifested an excellent aroma as set forth in Table II of Example XI, supra.

EXAMPLE XVI

Preparation of Soap Composition

One hundred grams of soap chips (IVORY ®, registered trademark of the Procter & Gamble Co. of Cincinnati, Ohio) are mixed individually with one gram each of the perfumery substances of Table II of Example XI, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table II of Example XI, supra.

EXAMPLE XVII

Preparation of a Solid Detergent Composition

A detergent is prepared from the following ingredients according to Example I of Canadian Letters Pat. No. 1,007,948 the specification for which is incorporated by reference herein):

| Ingredients | Parts by Weight |
| --- | --- |
| "Neodol 45-11" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table II of Example XI, supra. The detergent samples each have excellent aromas as set forth in Table II of Example XI, supra.

EXAMPLE XVIII

Utilizing the procedure of Example I at column 15 of U.S. Pat. No. 3,632,396, the specification for which is incorporated by reference herein, a non-woven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);
   57 percent $C_{20-22}$ HAPS
   22 percent isopropyl alcohol
   20 percent antistatic agent
   1 percent of one of the perfume substances of Table II of Example XI, supra.

A fabric softening composition prepared as set forth above having the above aroma characteristics as set forth in Table II of Example XI, supra, essentially consists of a substrate having a weight of about 3 grams per B 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table II of Example XI is imparted in a pleasant manner to the headspace in the dryer on operation thereof, using said dryer-added fabric softening non-woven fabric.

EXAMPLE XIX

The following liquid flavor formulation is prepared:

| Ingredient | Parts by Weight |
| --- | --- |
| Compound having the structure: 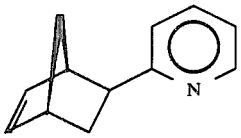 prepared according to Example I | 40.0 |
| Methoxy isobutyl pyrazine prepared according to the procedure of U.S. Letters Patent 3,630,750 the specification for which is incorporated by reference herein | 60.0 |

The resulting mixture is added to a 95% food grade aqueous ethanol solution at the rate of 3%. The resulting material is added to a "Green Goddess ® Salad Dressing" at the rate of 8 ppm of effective ingredient (that is mixture of compound having the structure:

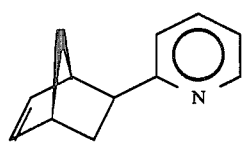

and methoxy isobutyl pyrazine). The addition of the compound having the structure:

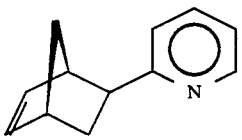

to the salad dressing imparts to it an excellent natural bell pepper, green vegetable, galbanum and floral aroma and taste profile. Without the compound having the structure:

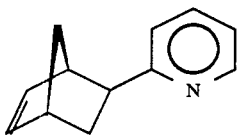

although a bell pepper flavor exists in the Green Goddess ® Salad Dressing flavor, it is not natural-like and does not have the intense green vegetable character that is imparted thereto by the compound having the structure:

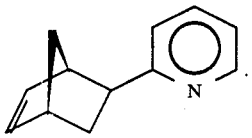

EXAMPLE XX

Cocoa Mix

At the rate of 0.1 ppm, the mixture of compounds defined according to the structure:

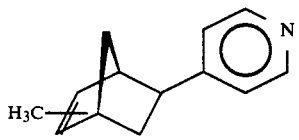

prepared according to Example VI is added to a 1.0 ounce serving of OVALTINE'S ® HOT'N RICH HOT COCOA MIX: Ingredients of OVALTINE'S ® HOT'N RICH HOT COCOA MIX:
Whey
Cocoa processed with alkali
Partially hydrogenated vegetable oil containing one or more of coconut oil, cotton seed oil, palm oil or soy bean oil
Corn syrup
Carob meal
Sugar
Tricalcium phosphate
Sodium chloride
Sodium caseinate
Dipotassium phosphate
Sodium citrate
0.27% sodium saccharin
Propylene glycol esters of fatty acids
Sodium silico aluminate
Vanillin
Ferric sodium pyrophosphate
Carrageenan
Lecithin
Ascorbic acid
Vitamin A palmitate
Niacin
Riboflavin
Thiamin OVALTINE'S ® HOT'N RICH HOT COCOA MIX is produced by Ovaltine Products, Inc., of Villa Park, Ill. 60181.

The mixture of compounds defined according to the structure:

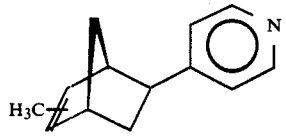

prepared according to Example VI provides a cinnamon-like bitter chocolate nuance which is long lasting, intense and causes the cocoa flavor to be very natural-like.

EXAMPLE XXI

The following orange jello cake mix is prepared:
1 Box yellow cake mix
¾ Cup orange juice
¾ Cup Wesson oil
4 Eggs
1 Small package of orange jello Prior to preparation, the orange juice is admixed at the rate of 0.5 ppm with the compound having the structure:

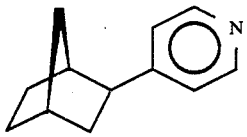

produced according to Example IV and at a rate of 0.5 ppm with a mixture of compounds defined according to the structure:

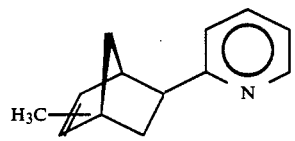

produced according to Example V.

The resulting materials are mixed by first mixing the cake mix, orange juice and salad oil. The eggs are added one at a time. After stirring, the jello is added. The resulting mixture is mixed thoroughly and baked in a greased, lightly floured tube cake pan approximately one hour at 350° F.

The resulting orange jello cake has an excellent natural orange flavor with an "orange-albedo" characteristic which is reminiscent of freshly picked oranges. The natural character, particularly the albedo character, is missing when the compounds having the structures:

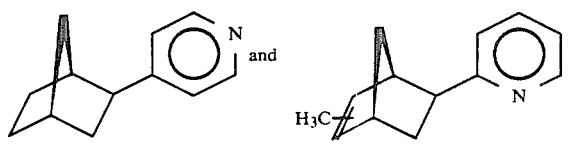 and are omitted from the cake mixture.

EXAMPLE XXIII

Pineapple Nut Cake

A pyrex dish (11 inches×13 inches) is greased and spread on the bottom with natural pineapple. Sugar is spread over the pineapple. One box of yellow cake mix is spread over the sugar. 1.5 sticks of butter are sliced and spread over the cake mix. Two cups of pecan nuts are placed over the resulting mixture. At the rate of 1.0 ppm an aqueous ethanolic (95% ethanol) solution of a 50:50 mixture of the compounds having the structure:

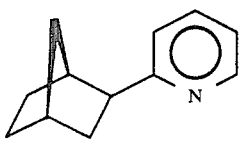

produced according to Example II and having the structure:

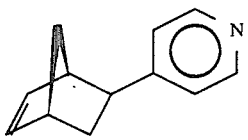

prepared according to Example III is added by means of sprinkling. After three minutes, the resulting product is baked at a temperature of 350° F. in an oven until the pecans almost burn . . . for a period of 45 minutes.

The resulting Pineapple Nut Cake has an excellent natural walnut taste in addition to the pineapple and pecan aroma and taste nuances. In the absence of the compounds having the structures:

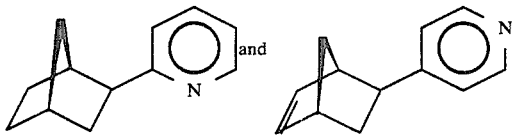

the resulting cake is missing the natural walnut-like nuances.

EXAMPLE XXIV

Raspberry Flavor Formulation

The following basic raspberry flavor formulation is produced:

| Ingredient | Parts by Weight |
| --- | --- |
| Vanillin | 2.0 |
| Maltol | 5.0 |
| Parahydroxybenzylactone | 5.0 |

-continued

| Ingredient | Parts by Weight |
| --- | --- |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| | 1000.0 |

This formulation is divided into two portions. To the first portion a mixture of compounds defined according to the structure:

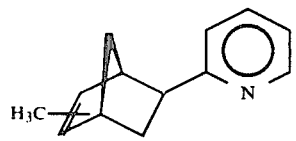

prepared according to Example V is added. To the second portion nothing is added.

The flavor containing the mixture of compounds defined according to the structure:

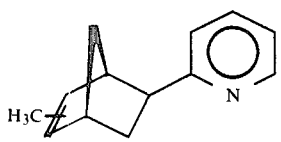

has a fresh "recently picked" raspberry aroma with raspberry kernel nuances when the mixture of compounds defined according to the structure:

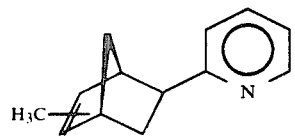

is added at the rate of 0.8 ppm.

The flavor containing the mixture of compounds defined according to the structure:

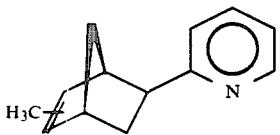

has a substantially and more pleasant and better raspberry aroma and taste profile. It the unanimous opinion of a bench panel of five members (not associated with the inventorship entity of the instant application and not associated with the assignee of the instant application) that the mixture of compounds defined according to the structure:

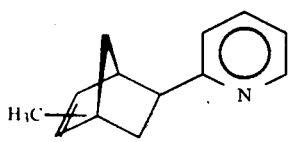

of our invention rounds the flavor out and contributes to a very natural fresh aroma and taste as found in full ripe raspberries which are recently picked. Accordingly, the flavor with the addition of the mixture of compounds defined according to the structure:

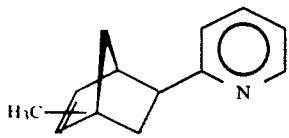

is unanimously considered to be substantially better than the flavor without the mixture of compounds defined according to the structure:

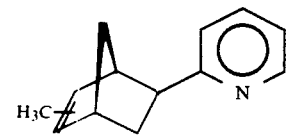

of our invention.

EXAMPLE XXV

A. Raspberry Flavor Formulation

20 Grams of the flavor formulation of Example XXIV containing the mixture of compounds defined according to the structure:

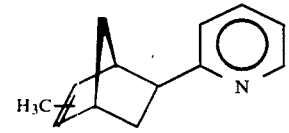

prepared according to Example V of our invention is emulsified in a solution containing 300 grams gum acacia and 700 grams of water. The emulsion is spray-dried with a Bowen Lab Model Drier utilizing 260 c.f.m. of air with an inlet temperature of 500° F. and an outlet temperature of 200° F. and a wheel speed of 50,000 rpm.

B. Sustained Release Flavor

The following mixture is prepared:

| Ingredients | Parts by Weight |
|---|---|
| Liquid raspberry flavor of Example XXIV | 20.00 |
| Propylene Glycol | 9.00 |
| Cab-O-Sil ® M-5 Brand of Silica produced by 125 High Street, Boston, Mass. 02110; Physical Properties: Surface Area: 200 m²/gm Nominal particle size: 0.012 microns | 5.00 |
| Density: 2.3 lbs./cu. ft. | |

The Cab-O-Sil ® is dispersed in each of the liquid raspberry flavor composition of Example XXIV (containing a mixture of compounds defined according to the structure:

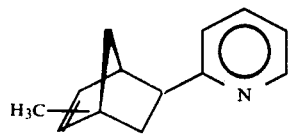

prepared according to Example V) with vigorous stirring, thereby resulting in a viscous liquid. 71 Parts by weight of the powder flavor composition of Part A, supra, is then blended into the said viscous liquid, with stirring, at 25° for a period of 30 minutes, resulting in a dry, free-flowing sustained release powder.

EXAMPLE XXVI

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of each of the liquid raspberry flavor composition of Example XXIV (containing a mixture of compounds defined according to the structure:

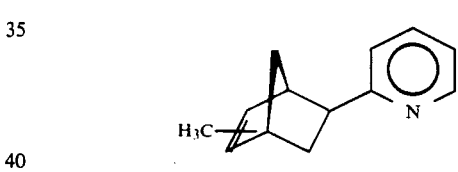

prepared according to Example V) is added to a solutions which are homogenized to form an emulsion having a particle size typically in the range of 5–40 microns. The material is kept at 120° F. under which conditions the gelatin will not jell.

Coacervation is induced by adding slowly and uniformly, 40 parts by weight of a 20% aqueous solution of sodium sulphate. During coacervation the gelatin molecules are deposited uniformly about each oil droplet as a nucleus.

Gelatin is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example is effected by washing with 200 parts by weight of 37% solution of formaldehyde in water. The cake is then washed to remove residual formaldehyde.

EXAMPLE XXVII

Chewing Gum

100 Parts by weight of chicle are mixed with 4 parts by weight of the flavor prepared in accordance with Example XXVI. 300 Parts of sucrose and 100 parts of corn syrup are added. Mixing is effected in a ribbon blender with jacketed walls of the type manufactured by the Baker Perkins Co.

The resultant chewing gum blends are then manufactured into strips 1 inch in width and 0.1 of an inch in thickness. The strips are cut into lengths of 3 inches each. On chewing, the chewing gum has a pleasant, long-lasting raspberry flavor.

EXAMPLE XXVIII

Chewing Gum

100 Parts by weight of chicle are mixed with 18 parts by weight of the flavors prepared in accordance with Example XXV(B). 300 Parts of sucrose and 100 parts of corn syrup are then added. Mixing is effected in a ribbon blender with jacketed walls of the type manufactured by the Baker Perkins Co.

The resultant chewing gum blends are then manufactured into strips 1 inch in width and 0.1 of an inch in thickness. The strips are cut into lengths 3 inches each. On chewing, the chewing gum has a pleasant, long-lasting raspberry flavor.

EXAMPLE XXIX

Toothpaste Formulation

The following separate groups of ingredients are prepared:

| Ingredient | Parts by Weight |
| --- | --- |
| Group "A" | |
| Glycerine | 30.200 |
| Distilled Water | 15.325 |
| Sodium Benzoate | .100 |
| Saccharin Sodium | .125 |
| Stannous | .400 |
| Group "B" | |
| Calcium Carbonate | 12.500 |
| Dicalcium Phosphate (Dihydrate) | 37.200 |
| Group "C" | |
| Sodium N—Lauroyl Sarcosinate (foaming agent) | 2.000 |
| Group "D" | |
| Flavor Material of Example XXV(B) | 1.200 |
| TOTAL | 100.000 |

Procedure

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-laurate sarcasinate.
5. The resultant slurry is then blended for one hour. The completed paste is then transferred to a three roller mill and then homogenized, and finally tubed.

The resulting toothpaste, when used in a normal toothbrushing procedure yields a pleasant raspberry flavor, of constant strong intensity throughout said procedure (1-1.5 minutes).

EXAMPLE XXX

Chewable Vitamin Tablets

The flavor material produced according to the procedure of Example XXV(B) is added to a chewable vitamin tablet formulation at a rate of 10 gm/kg, which chewable vitamin tablet formulation is prepared as follows:

In a Hobart Mixer, the following materials are blended to homogeneity:

| Ingredient | Gms/1000 Tablets |
| --- | --- |
| Vitamin C (ascorbid acid) as ascorbic acid-sodium ascorbate mixture 1:1 | 7.000 |
| Vitamin B$_1$ (thiamine mononitrate) as Rocoat ® thiamine monoitrate 33⅓% (Hoffman La Roche) | 4.000 |
| Vitamin B$_2$ (riboflavin) as Rocoat ® riboflavin 33⅓% | 5.000 |
| Vitamin B$_6$ (pyridoxine hydrochloride) as Rocoat ® pyridoxine hydrochloride 33⅓% | 4.000 |
| Niacinamide as Rocoat ® niacinamide 33⅓% | 33.000 |
| Calcium pantothenate | 11.500 |
| Vitamin B$_{12}$ (cyanocobalamin) as Merck 0.1% in gelatin | 3.500 |
| Vitamin E (di-alpha tocopheryl acetate) as dry Vitamin E acetate 33⅓% | 6.600 |
| d-Biotin | 0.044 |
| Flavor of Example XXV(B) | (as indicated above) |
| Certified lake color | 5.000 |
| Sweetener - sodium saccharin | 1.000 |
| Magnesium stearate lubricant | 10.000 |
| Mannitol q.s. to make | 500.000 |

Preliminary tablets are prepared by slugging with flatfaced punches and grinding the slugs to 14 mesh. 13.5 Grams dry Vitamin A Acetate and 0.6 grams Vitamin D are then added as beadlets. The entire blend is then compressed using concave punches at 0.5 grams each.

EXAMPLE XXXI

Chewing Tobacco

Onto 100 pounds of tobacco for chewing (85% Wisconsin leaf and 15% Pennsylvania leaf) the following casing is sprayed at the rate of 30%:

| Ingredient | Parts by Weight |
| --- | --- |
| Corn syrup | 60.0 |
| Licorice | 10.0 |
| Glycerine | 20.0 |
| Fig Juice | 4.6 |
| Raspberry flavor formulation of Example XXV(B) | 5.0 |

The resultant product is redried to a moisture content of 20%. On chewing, this tobacco has an excellent substantially consistent, long-lasting raspberry-like nuance, in conjunction with the tobacco notes.

EXAMPLE XXXII

CREST ® toothpaste (ordinary flavor) manufactured by the Procter & Gamble Co. of Cincinnati, Ohio, is intimately mixed at the rate of 1 ppm with a mixture of compounds defined according to the structure:

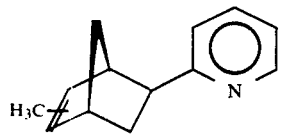

produced according to Example V. The resulting toothpaste on brushing gives rise to a fresh, natural, green, minty, natural orange taste profile which lasts during the entire brushing sequence (approximately two minutes).

What is claimed is:

1. A process for augmenting or enhancing the aroma or taste of a consumable material selected from the group consisting of foodstuffs, chewing gums, toothpastes and medicinal products comprising the step of adding to said consumable material from 0.5 parts per million up to about 100 parts per million based on the weight of said foodstuff of at least one compound defined according to the structure:

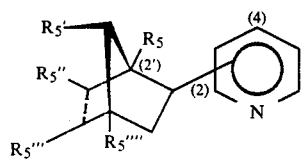

wherein $R_5$, $R_5'$, $R_5''$, $R_5'''$ and $R_5''''$ represent hydrogen or methyl; wherein the dashed line represents a carbon-carbon single bond or a carbon-carbon double bond; and wherein the norbornyl moiety is bonded to the pyridinyl moiety at the 2' position of the norbornyl moiety and the 2 or the 4 position of the pyridinyl moiety with the proviso that the substance added t the consumable material is a mixture when one of $R_5$, $R_5'$, $R_5''$, $R_5'''$ or $R_5''''$ is methyl.

2. A process for agumenting or enhancing the aroma or taste of a consumable material selected from the group consisting of foodstuffs, chewing gums, toothpastes and medicinal products comprising the step of adding to said consumable material from 0.5 ppm up to about 100 ppm by weight of said foodstuff of a product produced according to the process of intimately admixing a compound defined according to the structure:

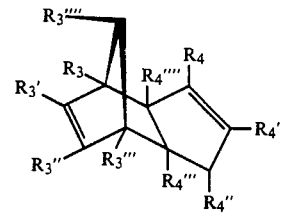

wherein one of $R_1$ or $R_2$ is vinyl and the other of $R_1$ or $R_2$ is hydrogen with the compound having the structure:

wherein one of $R_3$, $R_3'$, $R_3''$, $R_3'''$ and $R_3''''$ is methyl and the other of $R_3$, $R_3'$, $R_3''$, $R_3'''$ and $R_3''''$ represents hydrogen and wherein one of $R_4$, $R_4'$, $R_4''$, $R_4'''$ and $R_4''''$ represents methyl and the other of $R_4$, $R_4'$, $R_4''$, $R_4'''$ and $R_4''''$ reprsents hydrogen and heating the resulting mixture to reflux whereby the reaction:

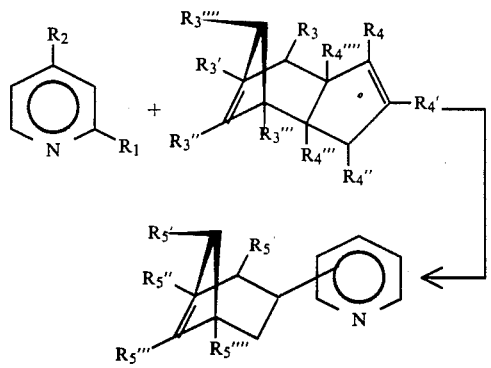

is carried out, thereby forming a mixture of compounds defined according to the structure:

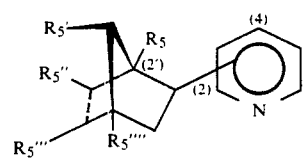

wherein one of $R_5$, $R_5'$, $R_5''$, $R_5'''$ and $R_5''''$ is methyl and the other $R_5$, $R_5'$, $R_5''$, $R_5'''$ and $R_5''''$ is hydrogen.

* * * * *